(12) United States Patent
Sussmane et al.

(10) Patent No.: US 11,154,742 B1
(45) Date of Patent: Oct. 26, 2021

(54) PORTABLE RESISTANCE EXERCISE DEVICE (PRED)

(71) Applicants: Jeffrey Brett Sussmane, Okatie, SC (US); Samantha Rachel Sussmane, Okatie, SC (US)

(72) Inventors: Jeffrey Brett Sussmane, Okatie, SC (US); Samantha Rachel Sussmane, Okatie, SC (US)

( * ) Notice: Subject to any disclaimer, the term of this patent is extended or adjusted under 35 U.S.C. 154(b) by 84 days.

(21) Appl. No.: 16/708,736

(22) Filed: Dec. 10, 2019

(51) Int. Cl.
| | | |
|---|---|---|
| *A63B 21/04* | (2006.01) | |
| *A63B 21/00* | (2006.01) | |
| *A63B 24/00* | (2006.01) | |
| *A63B 21/055* | (2006.01) | |
| *A61B 5/11* | (2006.01) | |

(52) U.S. Cl.
CPC .... *A63B 21/0428* (2013.01); *A63B 21/00072* (2013.01); *A63B 21/0557* (2013.01); *A63B 21/154* (2013.01); *A63B 21/4034* (2015.10); *A63B 21/4035* (2015.10);
(Continued)

(58) Field of Classification Search
CPC ........ A63B 21/00058; A63B 21/00069; A63B 21/00072; A63B 21/00076; A63B 21/02; A63B 21/04; A63B 21/0407; A63B 21/0414; A63B 21/0421; A63B 21/0428; A63B 21/0435; A63B 21/0442; A63B 21/055; A63B 21/0552; A63B 21/0555; A63B 21/0557; A63B 21/15; A63B 21/151; A63B 21/154; A63B 21/159; A63B 21/4027; A63B 21/4033; A63B 21/4034; A63B 21/4035; A63B 21/4045; A63B 24/0062; A63B 71/0009; A63B 2071/0018; A63B 2210/00; A63B 2210/50; A63B 2220/17; A63B 2220/50; A63B 2220/51;
(Continued)

(56) References Cited

U.S. PATENT DOCUMENTS 3,156,465 A * 11/1964 Jacobi ................... A63B 23/12
482/37
3,381,958 A * 5/1968 Gulland ............... A63B 22/001
482/96
(Continued)

FOREIGN PATENT DOCUMENTS

| GB | 2010101 A | * | 6/1979 | ........... A63B 21/018 |
| GB | 2012599 A | * | 8/1979 | ....... A63B 23/03575 |
| GB | 2027598 A | * | 2/1980 | ........... A63B 22/205 |

*Primary Examiner* — Gary D Urbiel Goldner
(74) *Attorney, Agent, or Firm* — Banner & Witcoff, Ltd.

(57) ABSTRACT

An exercise device is portable and lightweight, where a user pushes levers (for example, handles or pedals) in a linear fashion. The levers may not be connected to each other and may be used alternately or both at the same time. Each lever is connected to a bearing mechanism inside of a housing, where the bearing mechanism reduces friction and creates stability when pushing the levers. The levers are attached to one or more sets of resistance bands that enable different levels of resistance by rotating a top dial to vary the intensity of physical activity. The device has a base having foldable base supports and foldable pedals, thus providing portability of the device. The exercise device may have a pedometer situated within one of the levers that counts the steps and may communicate with an application executing on a mobile device in order to measure the user's exercise performance.

17 Claims, 21 Drawing Sheets

(52) U.S. Cl.
CPC ........... *A63B 24/0062* (2013.01); *A61B 5/112* (2013.01); *A63B 2210/50* (2013.01); *A63B 2225/52* (2013.01)

(58) Field of Classification Search
CPC ............ A63B 2220/58; A63B 2225/09; A63B 2225/093; A63B 2225/50; A63B 2225/52
See application file for complete search history.

(56) References Cited

U.S. PATENT DOCUMENTS

| | | | | |
|---|---|---|---|---|
| 4,149,713 A * | 4/1979 | McLeod | .......... | A63B 23/03533 482/101 |
| 4,284,272 A * | 8/1981 | Evans | .................. | A63B 21/154 482/72 |
| 4,540,172 A * | 9/1985 | Evans | .................. | A63B 21/018 482/120 |
| 5,000,441 A * | 3/1991 | Wang | ................. | A63B 22/0002 482/112 |
| 5,090,690 A * | 2/1992 | Huang | ............... | A63B 22/0002 482/131 |
| 5,295,927 A * | 3/1994 | Easley | ................ | A63B 21/015 482/51 |
| 5,299,995 A * | 4/1994 | Ko | ..................... | A63B 23/0417 482/52 |
| 5,441,255 A * | 8/1995 | Verbick | ............ | A63B 23/03508 473/422 |
| 5,480,367 A * | 1/1996 | Bergman | ........... | A63B 21/0552 482/122 |
| 5,803,880 A * | 9/1998 | Allen | ................. | A63B 21/0087 482/113 |
| 6,331,153 B1 * | 12/2001 | McClellan | ........... | A63B 22/205 482/52 |
| 7,086,997 B1 * | 8/2006 | Fields | .................. | A63B 69/004 482/83 |
| 9,283,428 B1 * | 3/2016 | Esrick | .............. | A63B 21/00069 |
| 10,179,260 B1 * | 1/2019 | Stearns | .............. | A63B 21/4045 |
| 10,434,362 B1 * | 10/2019 | Stevenson | ........... | A63B 24/0087 |
| 2004/0204293 A1 * | 10/2004 | Andreasen | ........ | A63B 21/00181 482/52 |
| 2005/0075182 A1 * | 4/2005 | Middleton | ........... | A63B 21/055 472/135 |
| 2005/0079956 A1 * | 4/2005 | Bruno | ................ | A63B 69/0022 482/51 |
| 2008/0261784 A1 * | 10/2008 | Osbak | ................ | A63B 21/4049 482/92 |
| 2009/0239720 A1 * | 9/2009 | Osbak | .............. | A63B 23/03525 482/112 |
| 2011/0070021 A1 * | 3/2011 | Huang | .................. | F16B 7/1418 403/374.5 |
| 2012/0129665 A1 * | 5/2012 | Walker | ............... | A63B 21/4045 482/139 |
| 2013/0331195 A1 * | 12/2013 | Sery | ................. | A63B 69/36213 473/223 |
| 2015/0343259 A1 * | 12/2015 | Mercenari Uribe | . | A63B 22/205 482/52 |
| 2017/0128767 A1 * | 5/2017 | Jolly | .................. | A63B 21/4003 |
| 2017/0157445 A1 * | 6/2017 | Young | .................... | A63B 21/22 |
| 2017/0182359 A1 * | 6/2017 | Baril | ................. | A63B 21/4011 |
| 2019/0009129 A1 * | 1/2019 | Liao Lai | ............ | A63B 22/0002 |
| 2020/0094106 A1 * | 3/2020 | Liu | .................... | A63B 23/0417 482/52 |
| 2020/0171346 A1 * | 6/2020 | Chen | .................... | A63B 22/205 482/52 |

\* cited by examiner

PORTABLE RESISTANCE EXERCISE DEVICE (PRED)

TECHNICAL FIELD

Aspects of the disclosure relate to an exercise device that enables a user to participate in physical activity.

BACKGROUND OF THE INVENTION

As most people would agree, there are many benefits of regular exercise and maintaining fitness. Benefits include increasing energy levels, improving muscle strength, maintaining a healthy weight, improving brain function, improving heart health, reducing risk of diabetes, sleeping better, and improving mental health. There is overwhelming evidence that people who lead active lifestyles are less likely to be ill and more likely to live long.

However, there are factors that may limit an individual from adequately exercising. Needless to say, an exercise apparatus that enables a person to properly exercise would be a benefit to the person.

SUMMARY OF THE INVENTION

An exercise device enables a user to exercise, where the user pushes two pedals in a linear fashion. The pedals may be separate of each other and may be used alternately or both at the same time. The device may be placed on the floor and these pedals may be pushed with the feet. The device may be placed on a more raised surface and be pushed with the hands. The pedals are connected to a resistance-reducing (bearing or mechanical) mechanism within a housing. The pedals may be attached to a pair of resistance bands that enables different levels of resistance by rotating a dial at the top of the housing in order to vary the intensity of physical activity of the legs or the shoulder/arms.

The device may have a base with foldable base supports and foldable pedals, thus providing portability of the device. The exercise device may also have a pedometer within one of the pedals that counts the steps performed by the user and may communicate with an application executing on a mobile device in order to measure the user's exercise performance.

With an aspect, an apparatus comprises a housing having one or more longitudinal openings along the housing, one or more (bearing or mechanical) mechanisms, one or more levers (for example, pedals or handles), and a resistance mechanism. A lever is connected to a bearing mechanism so that the lever travels linearly along the longitudinal opening when a user pushes the lever. The resistance mechanism is connected to the bearing mechanism so that resistance is applied as the lever is moved.

With an aspect, a housing of an apparatus has a bottom edge with a desire angle and a plurality of mounting components to accommodate corresponding support elements.

With an aspect, a bearing mechanism comprises inner and outer sliding components and inside and outside braces. The inside brace has a protrusion that extends through openings of the inner and outer sliding components and that is attached to the outside brace. The lever is also attached to the outside brace.

With an aspect, an exercise apparatus may be used during an exercise workout where a user repetitively pushes down on one or more pedals (for example, two pedals) to achieve a desired amount of exercise (for example, as measured by a number of repetitions and/or a number of calories). The exercise apparatus may also be used for physical therapy, where a user (for example, a patient) exercises during a physical therapy session.

With an aspect, an exercise apparatus may comprise one or more handles to accommodate a user pushing down the handles with the user's hands.

With another aspect, levers (for example, pedals or handles) move separately (independently) of each other. Consequently, the levers may be used alternately or both at the same time.

With another aspect, an exercise apparatus may have a single lever (pedal or handle). The exercise apparatus may be tailored for situations encountered during physical therapy sessions, where a user (patient) has an injury to a leg and/or arm.

With another aspect, a housing of an exercise apparatus comprises inside and outside pads on which bearing mechanism contacts as a pedal moves in a linear fashion. The pads may comprise a material that has a smaller coefficient than the housing in order to reduce the degree of friction.

With another aspect, an exercise apparatus comprises a base mechanism having a plurality of base supports, where each base support is attached to the housing at a corresponding opening of the plurality of openings so that the physical exercise apparatus can be positioned at the desired angle. The base mechanism may further comprise a base hinge associated with each of the plurality of base supports, where each said base support is foldable against the housing.

With another aspect, a pedal is mounted to a bear mechanism via a pedal hinge, enabling the pedal to be foldable against a housing of an exercise apparatus.

With another aspect, an exercise apparatus provides resistance to a pedal via a resistance band. The resistance band is connected between an associated bearing mechanism and a mounting flange (which is situated on a threaded rod) via a pulley (which is mounted to an end cap). The amount of resistance provided by the resistance band may be adjustable by changing a distance between the end cap and the mounting flange.

With another aspect, a treaded rod is connected from a top dial (that is situated over the end cap) to the mounting flange through a hole in the end cap. As the top dial is rotated, the mounting flange moves along the thread rod within a housing. As the distance between the end cap and the mounting flange increases, the resistance offered to the pedal increases. Conversely, as the distance between the end cap and the mounting flange decreases, the resistance offered to the pedal decreases.

With another aspect, a physical exercise apparatus incorporates a pedometer at one of the pedals to count a number of steps taken by a user. The physical exercise apparatus may further include a computing device that obtains information about the counted steps and about a degree of resistance provided by a resistance bands and then sends this information to a mobile app via a wireless channel.

With another aspect, an exercise device may be portable and lightweight. The pedals are connected to a resistance-reducing bearing mechanism inside of a track within a cylindrical housing. The bearing mechanism and track reduce friction, reduce the cantilever effect of pedaling, and create stability when pushing the pedals. The pedals may be attached to one or more sets of resistance bands that enables different levels of resistance by rotating a device in the housing or a device in a top section in order to vary the intensity of physical activity. The device may have a base with foldable base supports and foldable pedals, thus providing portability of the device. The exercise device may also have a pedometer within one of the pedals that counts the steps and may communicate with an application executing on a mobile device in order to measure the user's exercise performance.

BRIEF DESCRIPTION OF THE DRAWINGS

The foregoing summary of the invention, as well as the following detailed description of exemplary embodiments of the invention, is better understood when read in conjunction with the accompanying drawings, which are included by way of example, and not by way of limitation with regard to the claimed invention.

DETAILED DESCRIPTION

Figure 1:
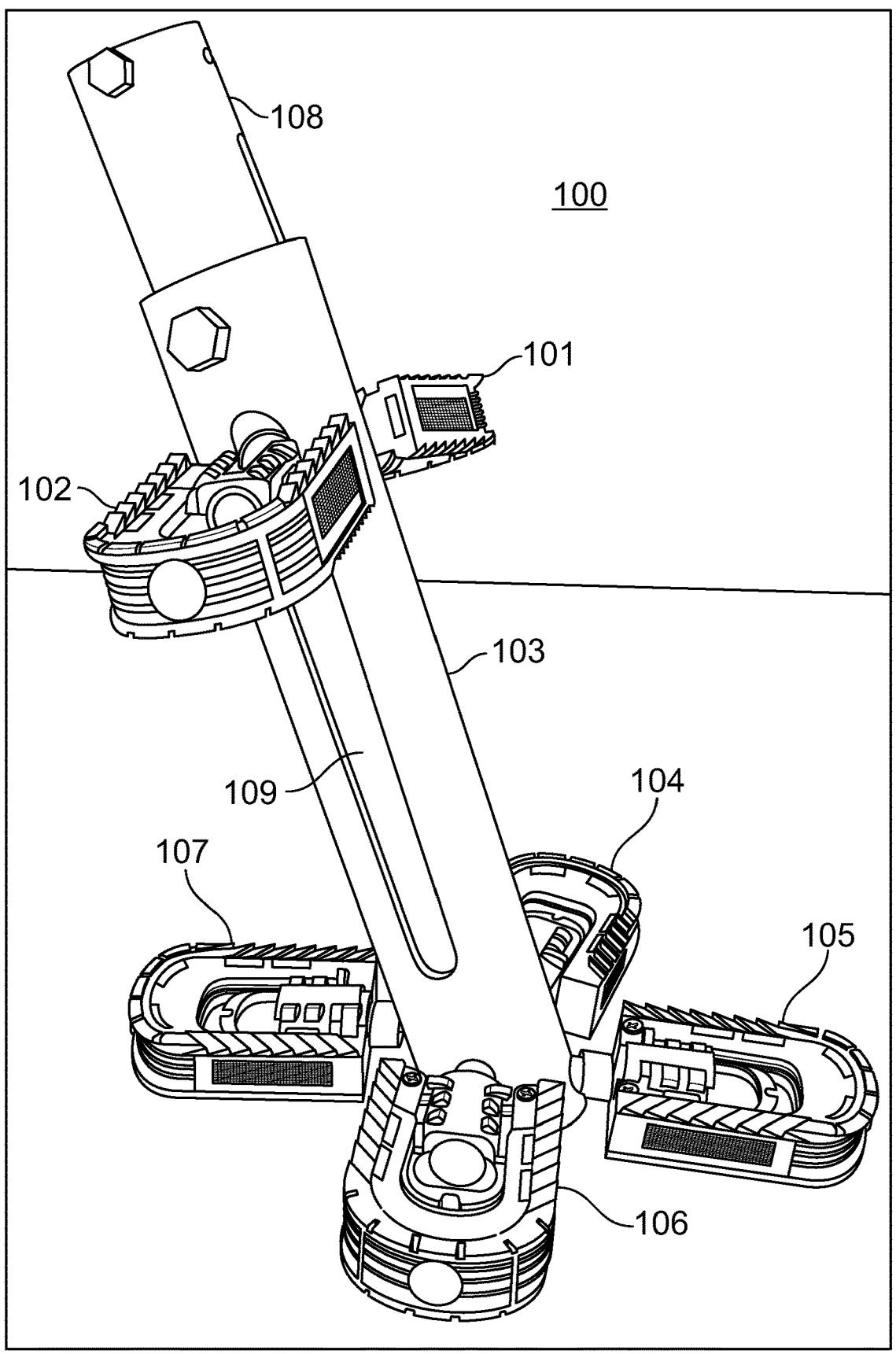
FIG. 1 shows an exercise device in accordance with an embodiment.

According to an aspect of the embodiments, an exercise device is portable and lightweight. The exercise device may have a pair of levers (for example, pedals or handles) that a user can push with the user's feet or arms in a linear fashion. The pedals or handles may be separate of each other and may be used alternately or both at the same time. The pedals or handles are connected to a bearing mechanism within a housing. The pedals or handles may be attached to one or more sets of resistance bands that enables different levels of resistance by rotating a top section in order to vary the intensity of physical activity.

According to an aspect of the embodiments, a portable resistance exercise device may be constructed primarily out of a molded but hollow cylinder. A small amount of metal may be required with some embodiments. The device may fold into a carrying sleeve and be light enough to be carried in a hand bag. This can be, but is not limited to, use at the office, home, rehabilitation/recovery, and traveling. The size, design and materials may be intended to allow for personal use in a car or airplane or other forms of seated travel. Alternate positions may allow for exercise of the arms with the use with the hands.

The portable resistance exercise device has attributes that may not be traditional approaches. These attributes may include:
  Portability of the device
  Collapsibility of the device
  Lightweight
  Easy to use
  Supports exercise for the legs
  Supports exercise for the arms
  Variable resistance exercise options
  Pedometer tracking capability
  Wireless software exercise evaluation
  Designed for personal use during car travel
  Designed for personal use during airline flight travel
  Designed for home use
  Designed for office use
  Designed for rehabilitation and recovery use
  Suitable for exercising by seniors who cannot exercise while standing There are portable exercise devices, according to traditional approaches. However, these devices do not collapse and are not as portable and self-contained as an umbrella.

The portable resistance exercise device, as discussed in the present patent application, is optimized for use when traveling. The device may be about the size of a portable collapsed umbrella and may weigh approximately three and one-half pounds. It can be carried and stored anywhere. The resistance exercise device may be designed primarily for the legs, and placed between the feet when seated. It is not typically designed to be used when standing or to support the full weight of the user. It easily opens and fits between the legs, when seated in a car, airplane, at home or at a desk. The device may be primarily designed to bring a workout to a seated person for as long as they wish to be seated. It may be used intermittently during trips or at work or home. The device may accommodate the use of the arms, by placing the device in front of the user and pushing down on the pedals (handles).

Exercise devices are most attractive when they are easy to use, readily available, convenient and customizable. Exercise devices are increasingly utilized when the effectiveness of the workout is maximized, and the time spent using the device is minimized. A person can make the most out of their time sitting with a workout, as intense as desired, for a short period of time, or easier, for a longer time. This device may also have a built-in pedometer. The is pedometer may be wirelessly connected to an application that also accommodates a mobile app. The app may be able to calculate various aspects of the workout including, but not limited to: number of steps taken, calories burned, time spent on the device, time spent doing different exercise intensities, distance, and so forth.

FIG. 1 shows exercise device (apparatus) 100 in accordance with an embodiment. Exercise device comprises pedals 101-102, lower cylindrical section 103, upper cylindrical section 108, and base supports 104-107. A user may physically exercise by pushing pedal 101 and/or pedal 102 in a linear movement along slot 109 and an opposite slot not visible in FIG. 1. The outside of sections 103 and 108 correspond to a lower cylindrical housing and an upper cylindrical housing, respectively.

Exercise device 100 may be designed to be portable and lightweight. With an embodiment, the total size of device 100 is approximately twelve-inch-long by three inches in diameter. Cylinder 103 is supported on the ground with four separate foldable base supports 104-107 that may collapse against cylinder 103. With an embodiment, cylinder 103 is approximately two inches in diameter. Base supports 104-107 add approximately one-half inch of additional diameter when folded against cylinder 103, making device 100 approximately three inches in diameter. Base supports 104-107 open out horizontally in four cardinal directions from the base, where each base support 104-107 opens to ninety degrees to each other. The size of base supports 104-107, when the base is fully opened on the ground, is approximately eleven inches in diameter.

With some embodiments, device 100 is designed to be used with the individual seated or semi-reclined. The bottom of the base/cylinder, when fully opened, is designed to rest at approximately a thirty-five degrees angle from vertical. Device 100 is not typically designed to support the user's weight or when standing.

Device 100 may also be used by a user pushing pedals 101-102 with his/her arms, but device 100 is not designed to support a user's body weight.

Figure 2:
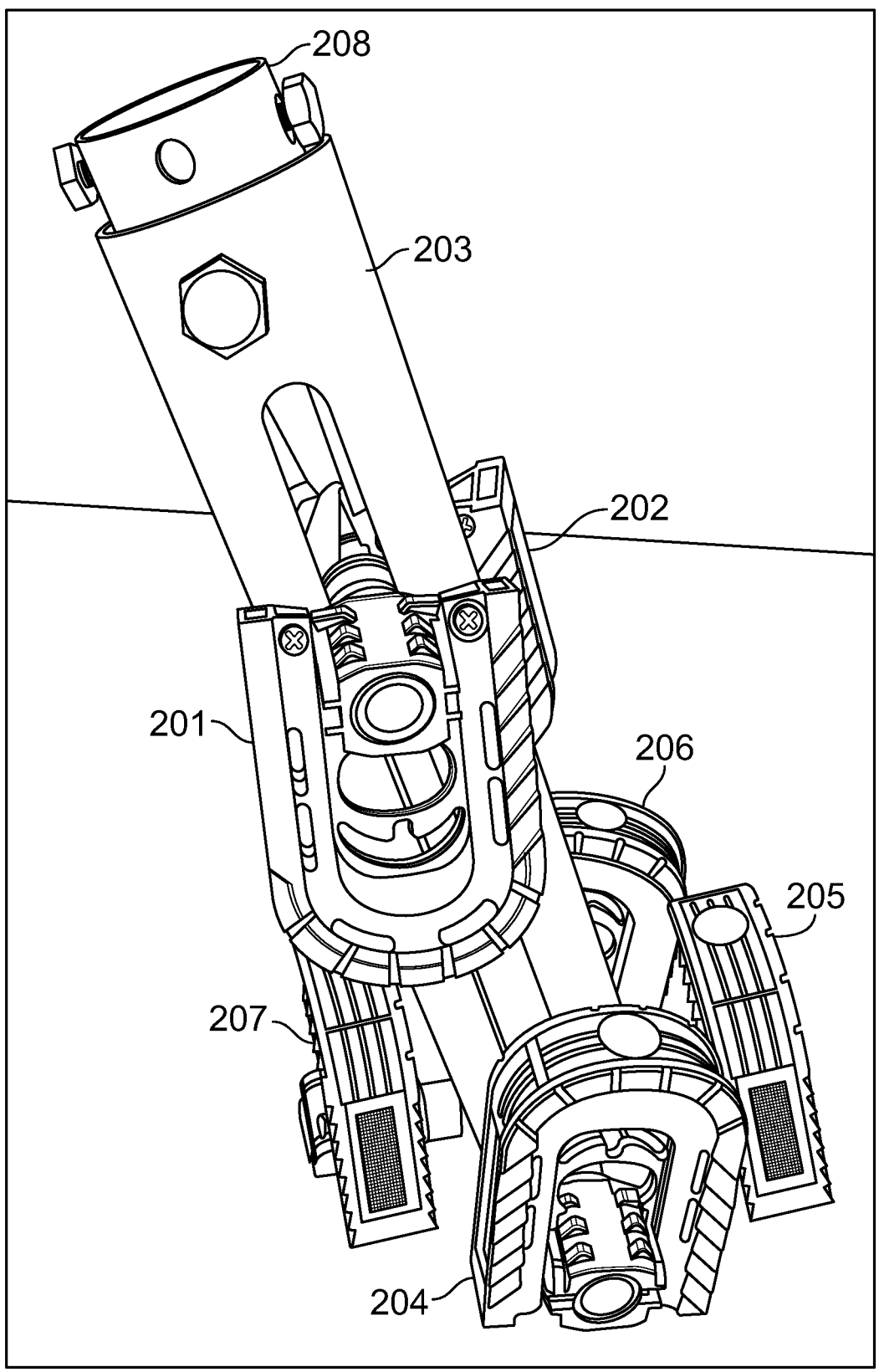
FIG. 2 shows the exercise device in a folding configuration in accordance with an embodiment.

Device has two foldable pedals 201-202 on either side (as shown in FIG. 2) that the user pushes for resistance exercise. Pedals 201-202 collapse against cylinder 203 for storage. Similarly, base supports 204-207 collapse.

Figure 13:
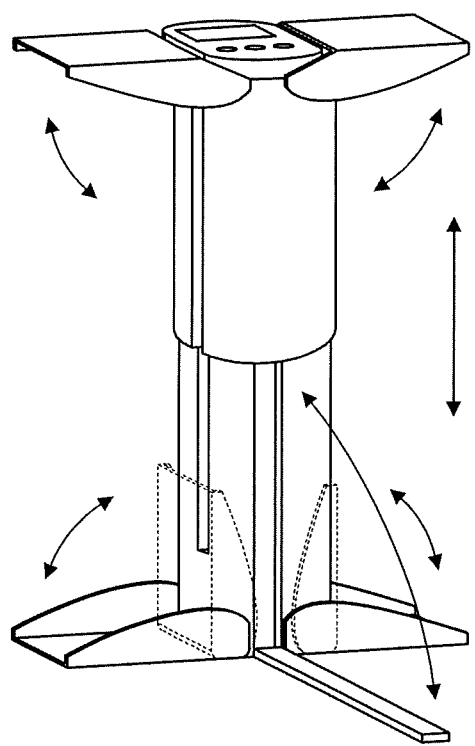
FIG. 13 shows an exercise device in accordance with an embodiment.
Figure 14:
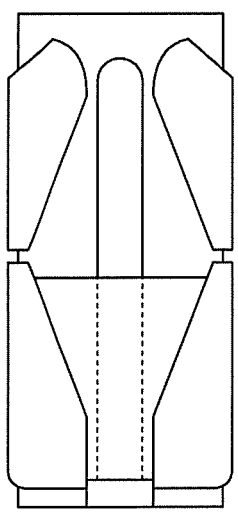
FIG. 14 shows the exercise device in a folding (or collapsed) configuration in accordance with an embodiment.

FIG. 13 shows another embodiment of an exercise device that may be folded as shown in FIG. 14.

Referring back to FIG. 1, a user typically does not use exercise device 100 while standing. However, some embodiments may accommodate a user by providing handles for the user to grip while in a standing position as the user pushes the pedals with the user's legs. Embodiments may incorporate a base/cylinder and a resistance mechanism that can accommodate the user's weight, where the cylinder is approximately perpendicular to the base.

Figure 3:
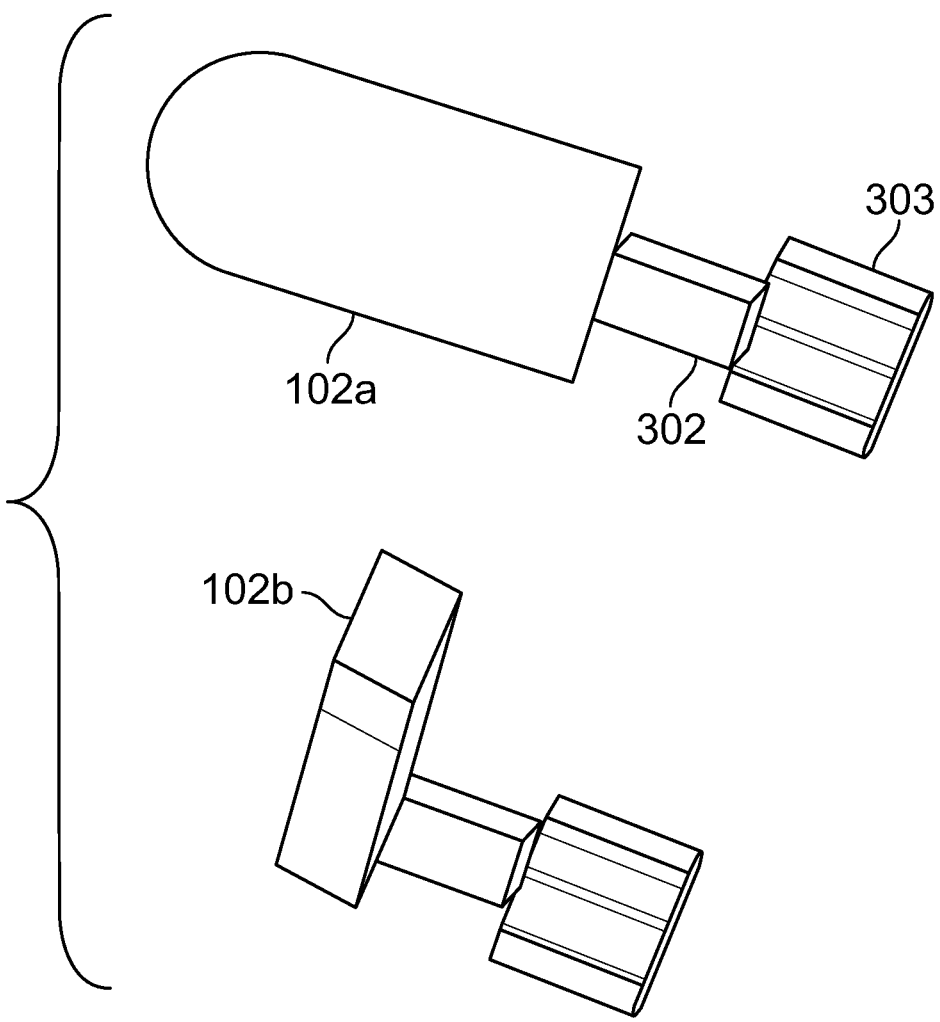
FIG. 3 shows foldable pedal in accordance with an embodiment.

FIG. 3 shows foldable pedal 102a-102b corresponding to pedal 101 as shown in FIG. 1. With an embodiment, pedal 102a-102b is approximately 4 inches long, 2 inches in width, and 0.5 inches in depth.

The pedal assembly shown in FIG. 3 also includes threaded base 303 and locking peg 302. As will be discussed, pedal 102-102b is secured to a bearing assembly by threaded base 303. Also, pedal 102a-102b may fold approximately 90 degrees in cooperation with peg 302.

Figure 4:
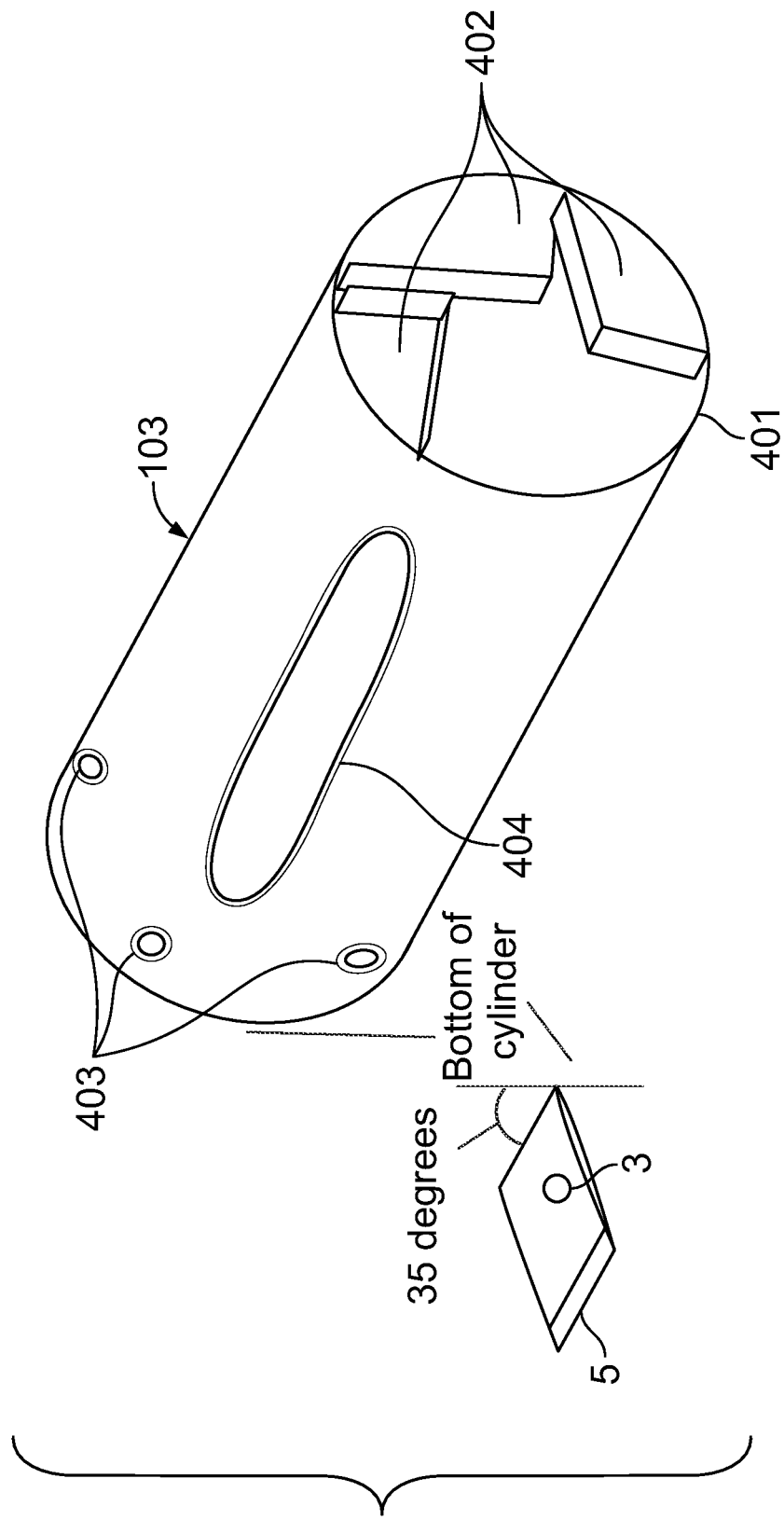
FIG. 4 shows a lower cylindrical housing of an exercise device in accordance with an embodiment.

FIG. 4 shows lower cylindrical housing 103 of exercise device 100 in accordance with an embodiment.

Lower cylindrical housing 103 has two parallel longitudinal oval cuts at two cardinal positions of 180 degree (one of which is shown as longitudinal cut 404 in FIG. 4). With an embodiment, longitudinal cut 404 is approximately 9 inches long, 0.5 inches wide, and 1.5 inches from the top and bottom of lower cylindrical housing 103.

With some embodiments, the bottom of lower cylindrical housing 103 may be designed at an angle of approximately 35 degrees from the vertical.

With some embodiments, inside walls 402 of top 401 of lower cylindrical housing 103 have three graduated steps (levels). This enables upper section 108 (shown in FIG. 1) to climb up the inside of cylinder 103 as upper section 108 is rotated to adjust resistance bands as will be discussed. The levels may begin and graduate at each of three ninety-degree cardinal positions. However, embodiments may support a different number of one or more graduated steps.

With some embodiments, lower cylindrical housing 103 has four holes 403 (approximately 0.5 inches in diameter) at cardinal positions of ninety degrees cut at the bottom of lower cylindrical housing 103. Base supports 104-107 may be attached to lower cylindrical housing 103 via holes 403.

Figure 5:
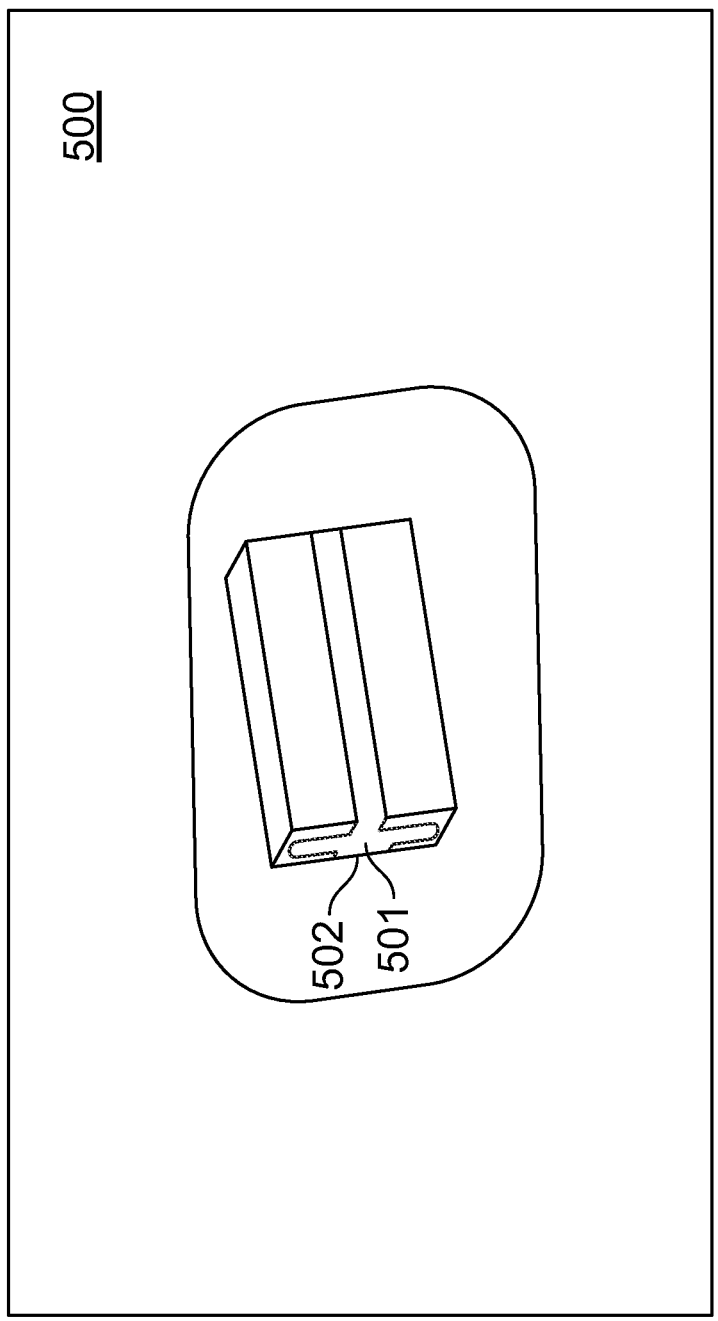
FIG. 5 shows an inside bearing track in accordance with an embodiment.

FIG. 5 shows a cross section of inside bearing track 500, where only one longitudinal cut (track) 501 is shown. However, inside bearing track 500 typically has two longitudinal cuts that allows linear movements of corresponding pedals 101-102 via a bearing mechanism that will be discussed. The two longitudinal cuts are at cardinal positions, opposite and parallel and are separated by approximately 180 degrees.

With some embodiments, inside bearing track 500 may be a cylinder inserted within lower cylindrical housing 103 or may be molded with lower cylindrical housing 103.

The longitudinal cuts are exposed to the pedal assemblies through center cuts (one of which is shown as center cut 502) that mate with slot 109 (as shown in FIG. 1). However, with some embodiments, center cut 502 may be slot 109 itself With an embodiment, track 501 is approximately 9 inches long, 3 inches wide and 0.75 inches deep. The center cut 502 is approximately 0.5 inches along track 501.

Figure 6:
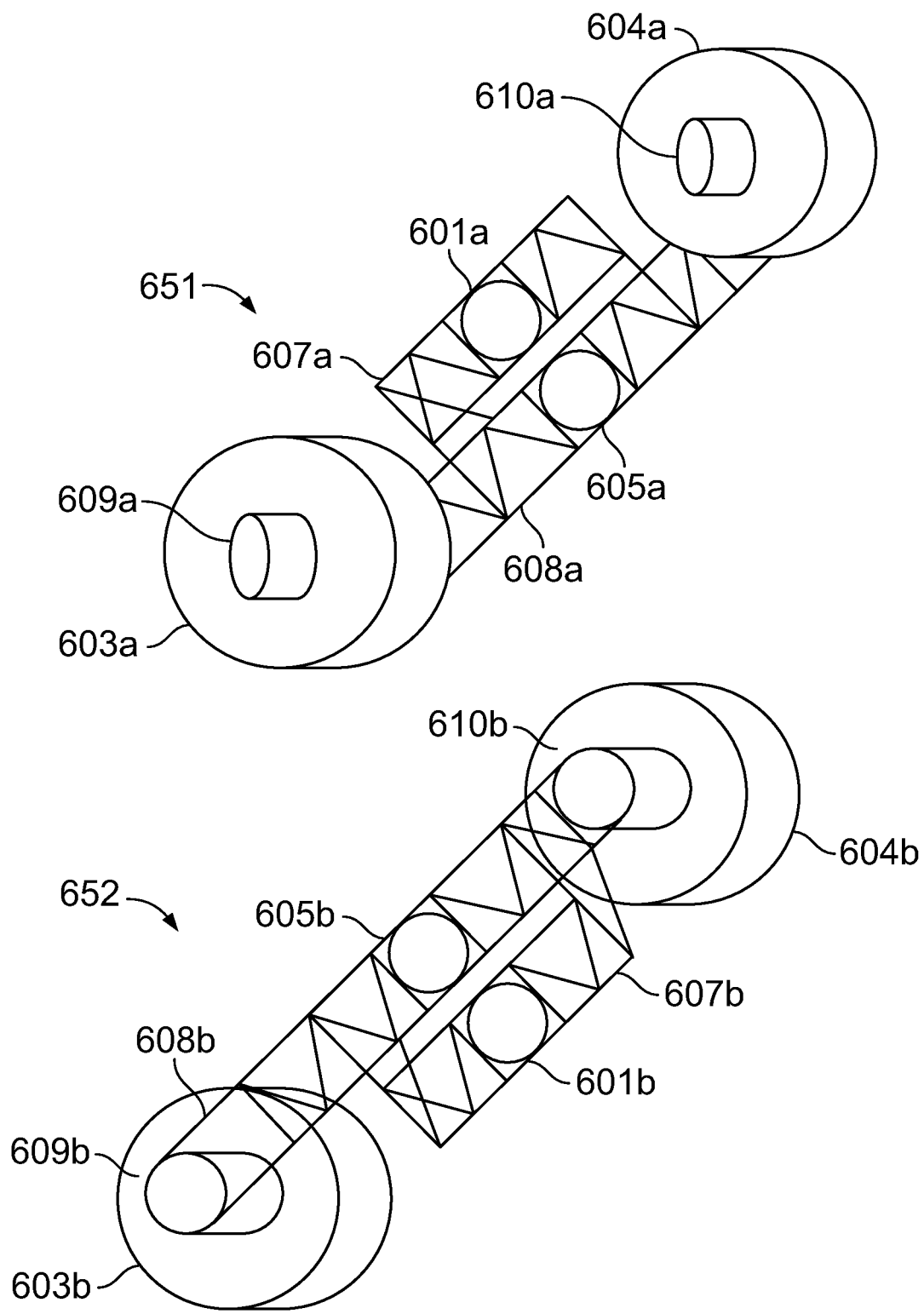
FIG. 6 shows a bearing mechanism in accordance with an embodiment.

FIG. 6 shows front view 651 and back view 652 of a bearing mechanism. Each pedal 101,102 (as shown in FIG. 1) is connected to a separate bearing mechanism to enable a user to push pedals 101 and 102 in a linear movement.

Pedals 102 and 101 act as cantilevers as a user pushes down on the pedals, resulting in lateral forces and causing the sides of bearings 603a,603b and 604a,604b against the sides of the associated tracks. The effectiveness of bearing mechanism 651,652 reduces friction and creates stability along associated tracks when pushing the pedals 101 and 102 is adversely affected by the lateral forces.

The resulting lateral forces of pedaling or pushing the pedals (handles) impedes a smooth motion along the tracks. The resulting phenomenon may be referred to as a cantilever effect. A cantilever brace, comprising outside portion 607a, 607b and inside portion 608a,608b, ameliorates the cantilever effect. FIG. 6 shows a 3-D perspective of the cantilever brace, where outside portion 607a,607b and inside portion 608a,608b align to axials 609a,609b and 610a,610b. A pedal (not explicitly shown in FIG. 6) is secured to the cantilever brace via sockets 601a,601b and 605a,605b, where socket 601a,601b and 605a,605b mate together. Consequently, axials (pedals/handles) 609a,609b and 610a,610b are constrained by the cantilever brace to be essentially perpendicular to the corresponding track. Inside portion 608a,608b is secured to the inside of bearing pair 609a,609b and 610a,610b but outside portion 607a,607b is not secured to the outside of the bearing pair. Consequently, the cantilever brace and bearing mechanism further reduce the cantilever effect and friction.

Referring back to the embodiment shown in FIG. 1, pedals 101-102 are not connected to each other and may be used alternately or both at the same time. Pedals 101-102 may be connected to a corresponding bearing mechanism within lower cylindrical housing 103.

With an embodiment, bearing axials 609a,609b and 610a, 610b are approximately two inches apart on center. The outside portions 609a and 610a of the axials extend approximately 0.25 inches while the outside portions 609b and 610b of the axials extend approximately 1.0 inches.

With some embodiments, a cantilever brace may comprise a solid structure having a width of approximately 0.25 inches and length of approximately one inch. The cantilever brace attach to the inside axials of the bearing mechanism.

Pedals 101 and 102 may be attached to one or more sets of resistance bands. The different sets of bands are attached to pedals 101 and 102 to provide for the option for different resistance exercises. The other ends of the resistance bands are attached to top section 108 of device 100.

Figure 7:
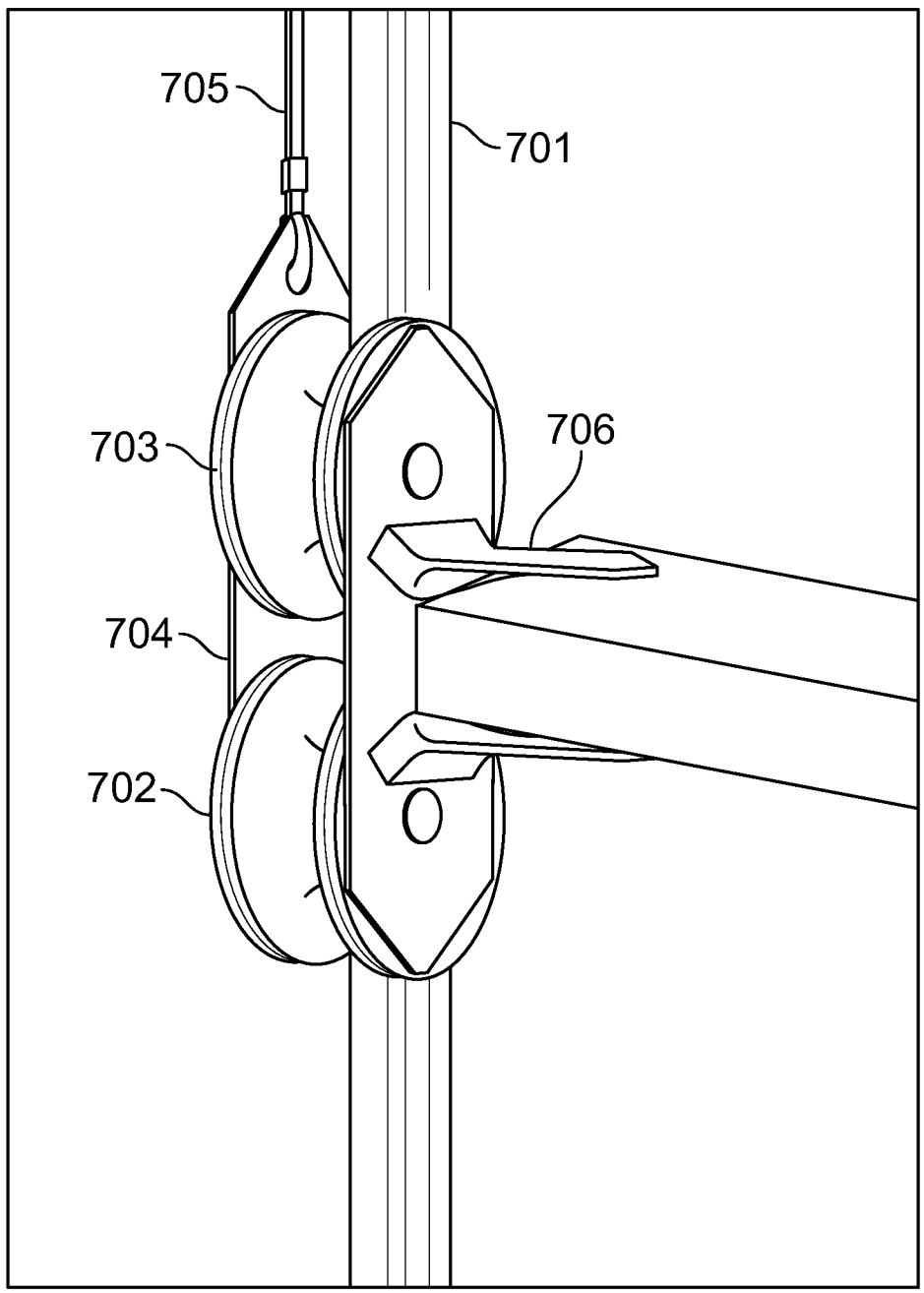
FIG. 7 shows a bearing mechanism engaged in a track in accordance with an embodiment.

Referring to FIG. 7, pedal 706 is attached in the middle of bearing mechanism that comprises bearing pair 702-703 and cantilever brace 704 and that travels along track 701. Resistance band 705 may be attached to the inside of the bearing mechanism as shown in FIG. 7.

With an embodiment, the lightest resistance band is always engaged when using device 100. The basic usage is light resistance. An additional set of resistance bands may be located inside cylinder 103. The additional set may be engaged by twisting top section 108 on the cylinder. Each additional twist of the top increases the resistance, thus giving the user variable options for the difficulty of their workout. The additional set of bands are attached to the rotating top 1001 via cable 1101 as will be further discussed with FIGS. 10-11. The resistance is increased when the user twists top 1001 (corresponding to section 108 as shown in FIG. 1) in defined increments of one quarter turn in conjunction with inside wall 402 as shown in FIG. 4. Inside threads may only allow twisting in one direction. Twisting top 1001 may disengage the threads back to neutral and may disengage the additional resistance set of bands.

Figure 8:
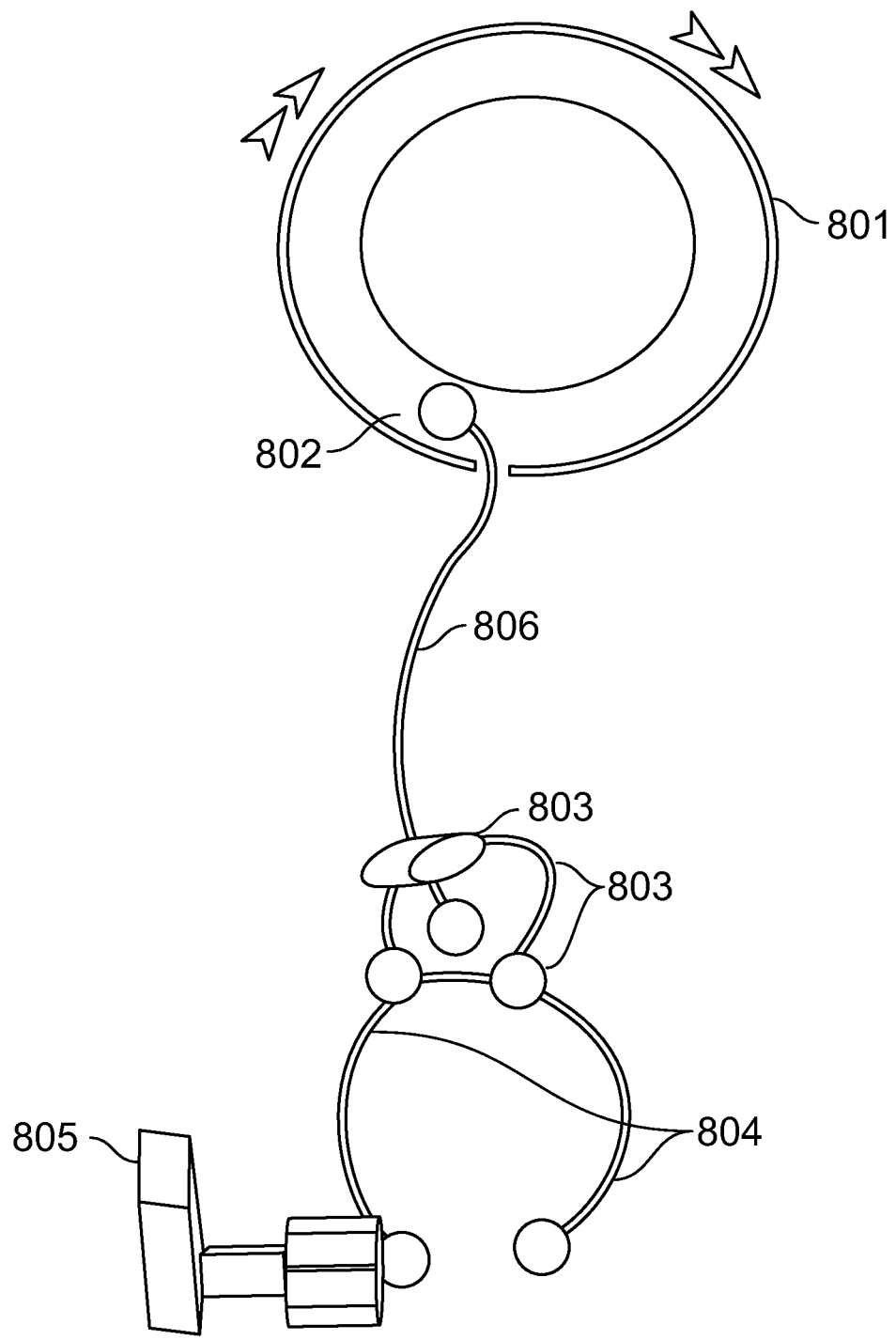
FIG. 8 shows a resistance mechanism attached to a pedal in accordance with an embodiment.
Figure 10:
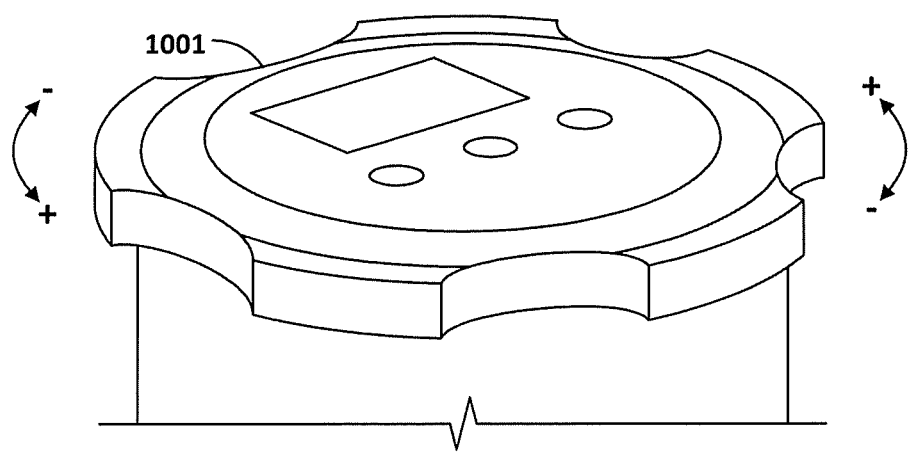
FIG. 10 shows a turning mechanism at the top of an exercise device in accordance with an embodiment.

FIG. 8 shows a resistance mechanism attached to pedal 805 in accordance with an embodiment. Top 801 (corresponding to top 1001 as shown in FIG. 10) rotates approximately 270 degrees in one direction. Cable 806 securely attaches to secondary resistance bands 804 at junction 803 and attaches to top 801 at junction 802.

Figure 9:
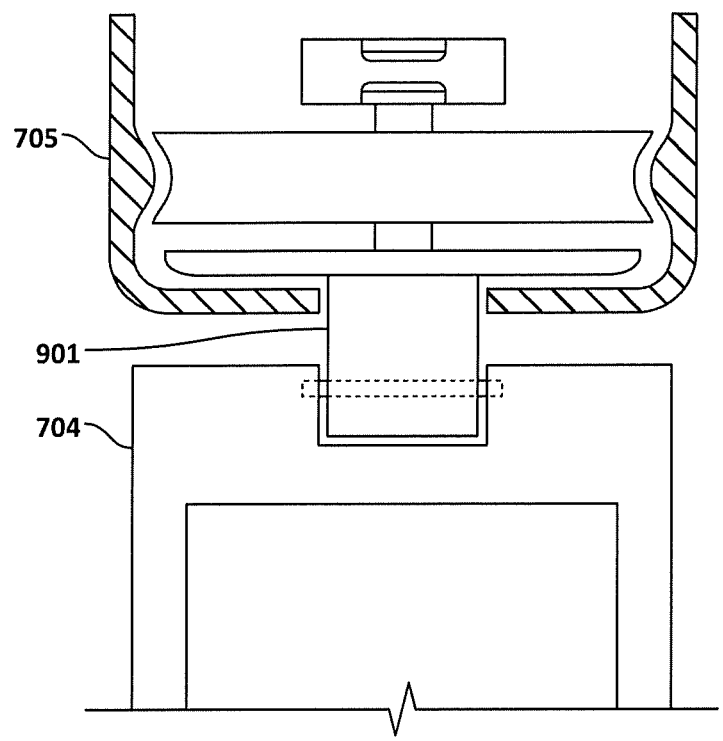
FIG. 9 shows a resistance band that is attached to an inside of a bearing mechanism in accordance with an embodiment.

FIG. 9 shows resistance band 705 (also shown in FIG. 7) that is attached to an inside of bearing mechanism 704 via ferrule attachment 901.

FIG. 10 shows turning dial 1001 at the top of exercise device 100 in accordance with an embodiment.

Figure 11:
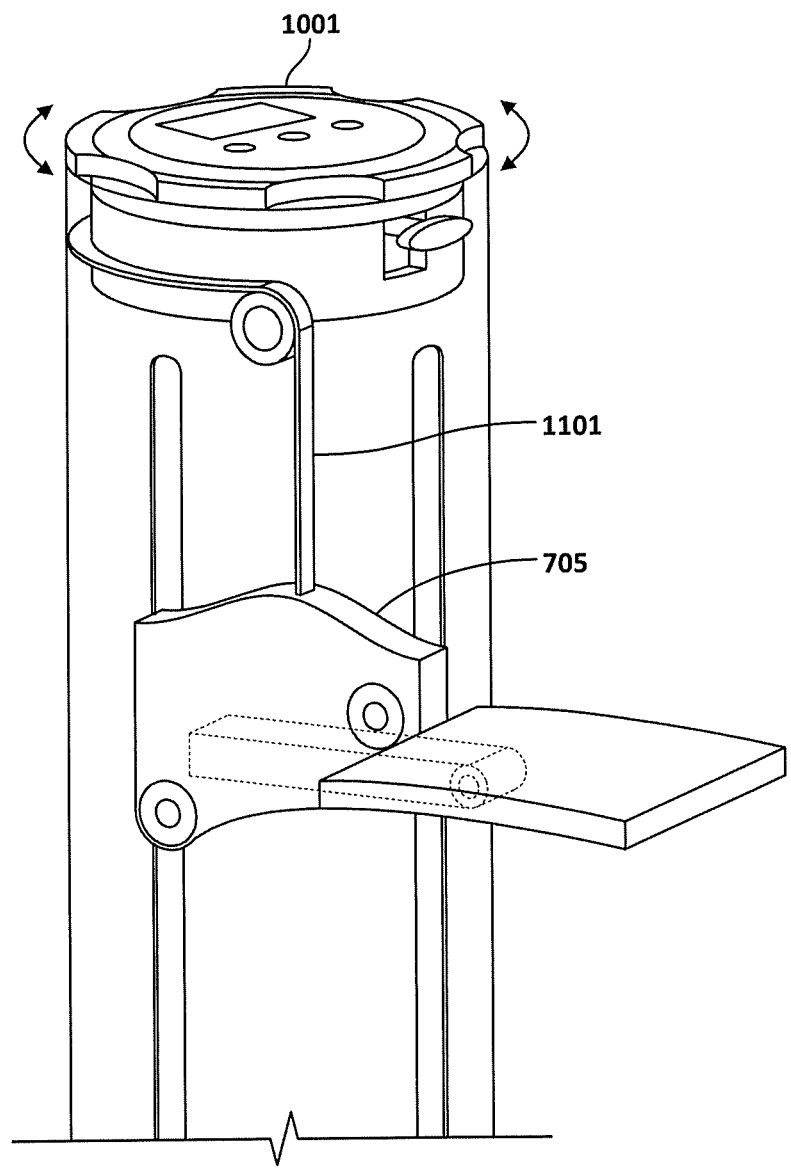
FIG. 11 shows a cable turning up into a turning dial in accordance with an embodiment.

FIG. 11 shows cable 1101 turning up into turning dial 1001 in accordance with an embodiment. Cable 1101 is attached to a set of two resistance bands. One band is attached to each pedal. One of the two bands (band 705 of FIG. 7) is shown in FIG. 11.

Figure 12:
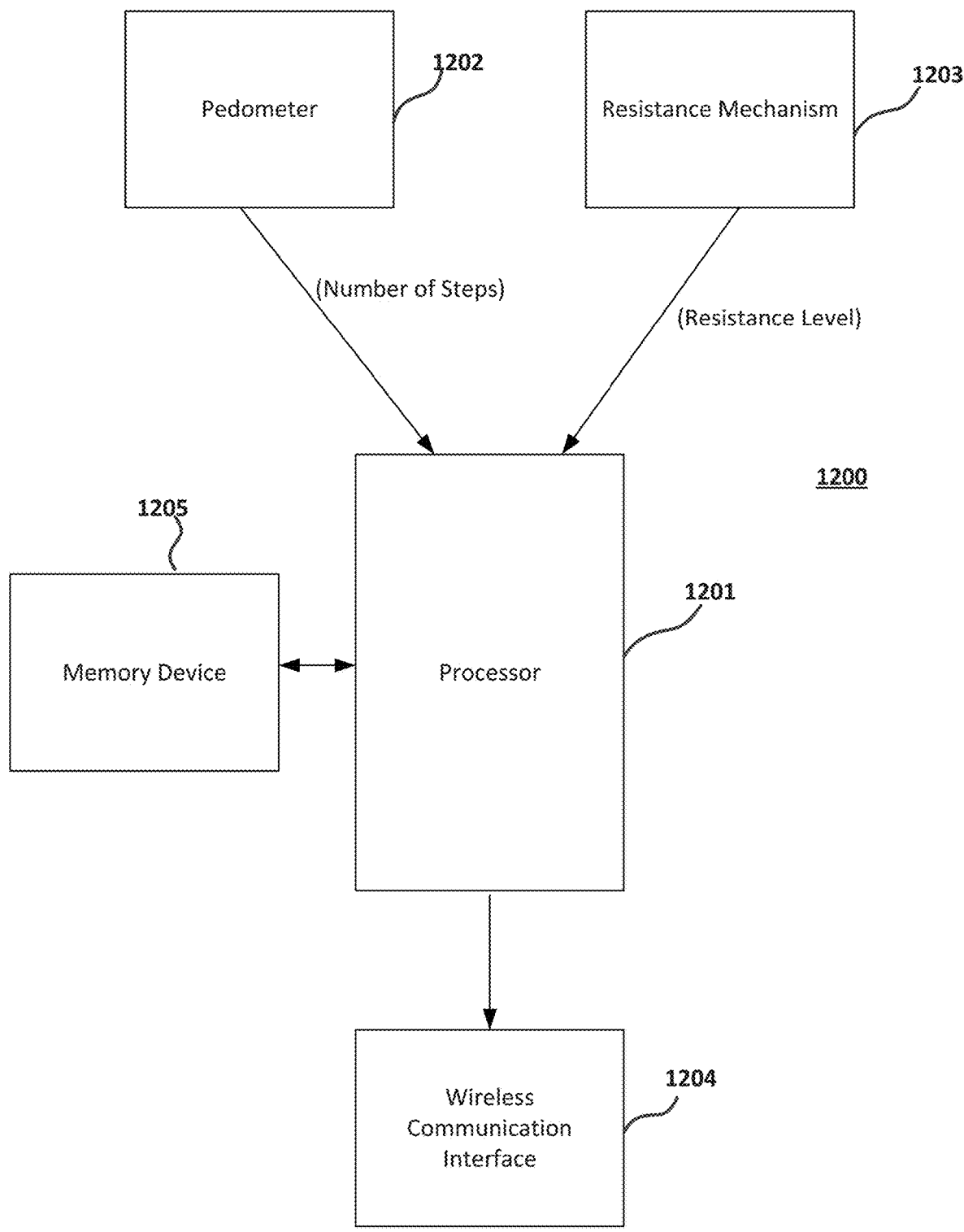
FIG. 12 shows a computing system for assessing a user's exercise performance in accordance with an embodiment.

FIG. 12 shows computing system 1200 for assessing a user's exercise performance in accordance with an embodiment.

With some embodiments, pedometer 1202 is located within one of the pedals that counts the steps and may communicate with an application (app). This app may be used on a mobile device or computer/tablet. Pedometer 1202, in conjunction with the app (not explicitly shown), may be used to measure the individual's exercise performance.

Processor 1201 may communicate with pedometer 1202 and resistance mechanism 1203, via wired or wireless connections, to obtain the number of steps by the user and the level of resistance, respectively. Processor 1201 may transmit this information over a wireless communication channel via wireless communication interface 1204 to a mobile device that is executing an app. The app may further process the above information in conjunction with the user's medical measurements (for example, heart pulse rate and breathing rate) to assess the level of physical activity for the user.

With reference to FIG. 12, a computing system environment may include a computing device where the processes discussed herein may be implemented. The computing device may include processor 1201 for controlling overall operation of the computing device and its associated components, including RAM, ROM, communications module, and memory device 1205. The computing device typically includes a variety of computer readable media. Computer readable media may be any available media that may be accessed by computing device and include both volatile and nonvolatile media, removable and non-removable media. By way of example, and not limitation, computer readable media may comprise a combination of computer storage media and communication media.

Computer storage media may include volatile and nonvolatile, removable and non-removable media implemented in any method or technology for storage of information such as computer readable instructions, data structures, program modules or other data. Computer storage media include, but is not limited to, random access memory (RAM), read only memory (ROM), electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by the computing device.

Communication media typically embodies computer readable instructions, data structures, program modules or other data in a modulated data signal such as a carrier wave or other transport mechanism and includes any information delivery media. Modulated data signal is a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

With some embodiments, processor 1201 may execute computer-executable instructions stored at memory 1205.

Figure 15:
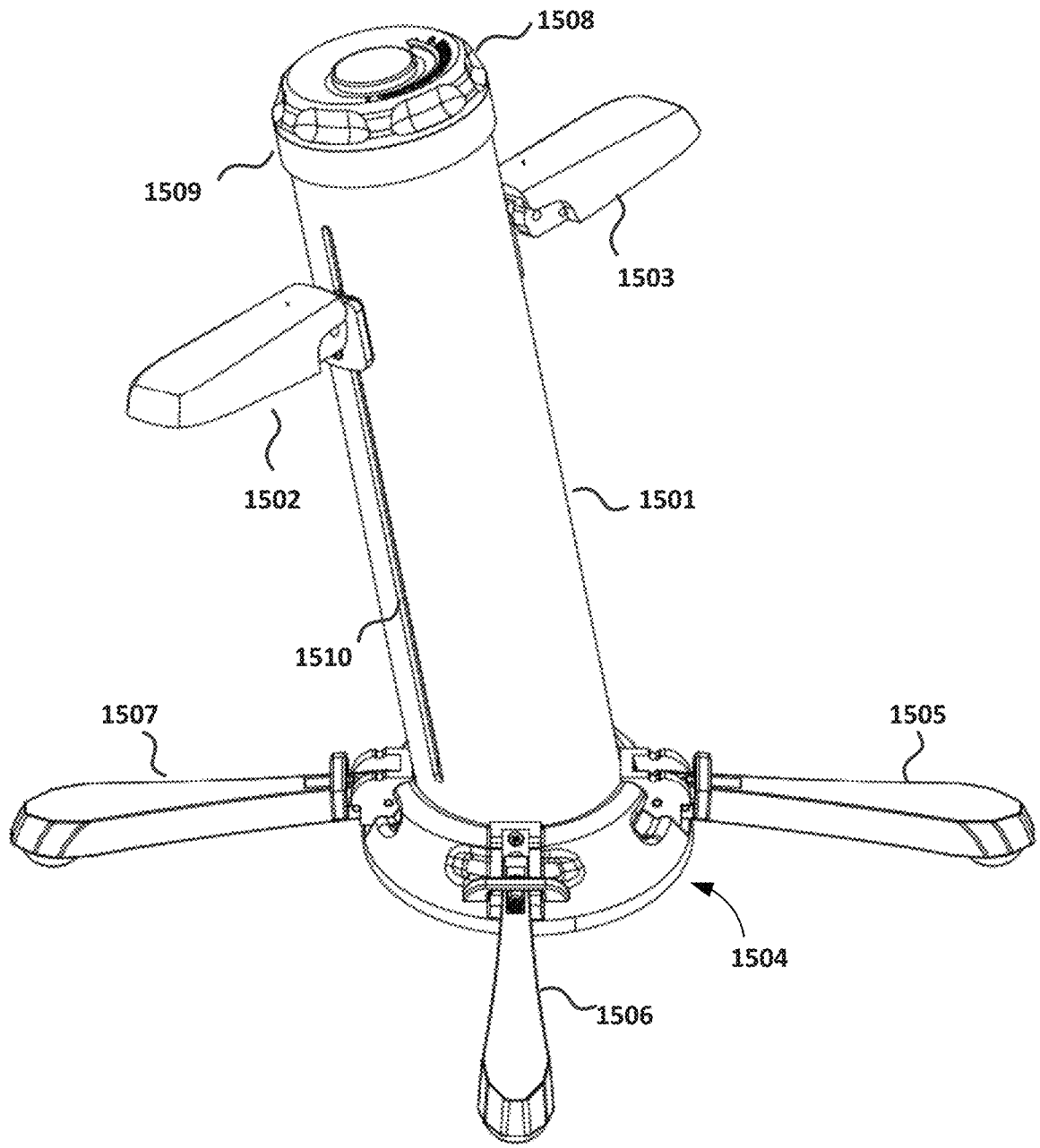
FIG. 15 shows an exercise device in accordance with an embodiment.

FIG. 15 shows exercise device 1500 in accordance with an embodiment. Exercise device 1500 comprises housing 1501 having a first longitudinal opening 1510 and a second longitudinal opening (not explicitly shown). A user can push down on pedals 1502 and 1503 (typically using one's feet) so that the pedals travel along the longitudinal openings. As will be discussed, when the user pushes down on a pedal (for example, pedal 1502), the pedal will return to its resting location by an attached resistance band not explicitly shown. Also, pedals 1502 and 1503 move independently of each other so that one or both pedals can be pushed by the user.

While housing 1501 has a cylindrical shape as shown in FIG. 15, embodiments may support different shapes (for example, cuboidal).

Exercise device 1500 rests on base 1504 so that device 1500 is positioned at a desired angle to that the user can comfortably exercise. For example, the user may place device 1500 on a floor and exercise by moving pedals 1502 and 1503 while sitting next to device 1500. Base 1504 may include a plurality of base supports (for example, four). As shown, base supports include supports 1505-1507.

As will discussed later in greater detail, exercise device 1500 includes top dial 1508 that allows the user to adjust the degree of resistance applied to pedals 1502 and 1503 in order to change the level of physical exertion while exercising.

Exercise device 1500 also includes end cap 1509 that enables one or more pulleys to be mounted. As will be discussed, the one or more pulleys allow for movement of resistance bands, which provide resistance to pedals 1502 and 1503.

While FIG. 15 shows pedals 1502 and 1503, different types of levers may be supported. For example, embodiments may support handles rather than pedals so that the user can push down on the levers with one's hands.

Because pedals 1502 and 1503 move independently of each other, a user can push on one or both pedals 1502 and 1503. Consequently, the user can exercise using one or both legs. This flexibility enables embodiments to be tailored for physical therapy applications. Moreover, embodiments may support a single lever (in other words, a single pedal or handle).

Figure 16:
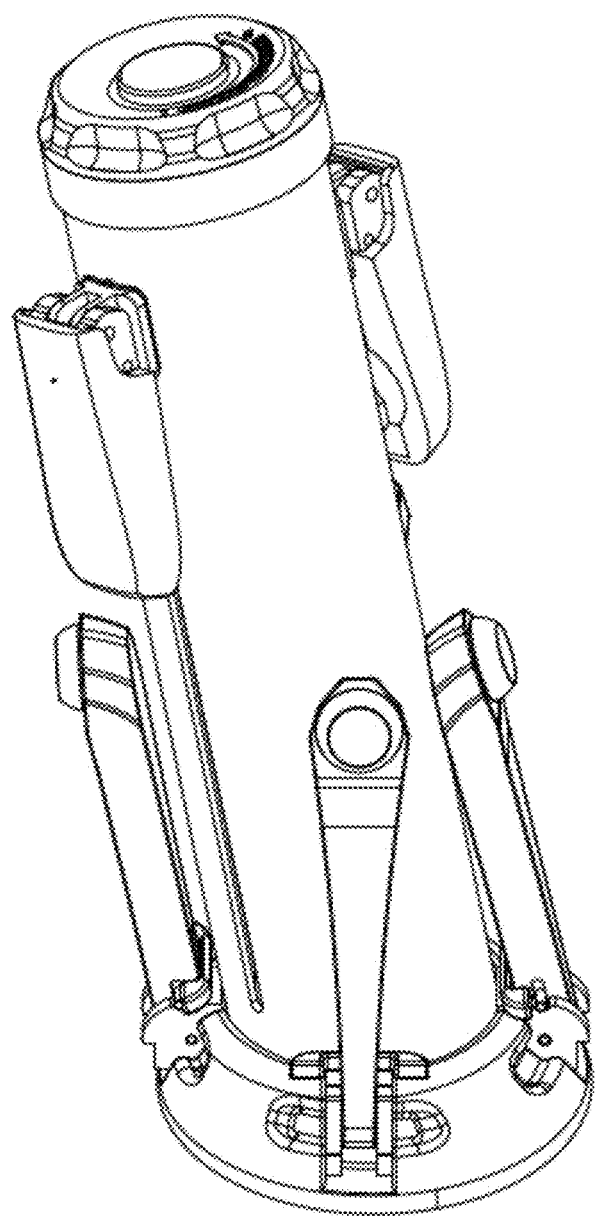
FIG. 16 shows the exercise device (as shown in FIG. 15) when folded (collapsed) in accordance with an embodiment.

FIG. 16 shows the exercise device (as shown in FIG. 15) when folded (collapsed) in accordance with an embodiment.

Figure 17:
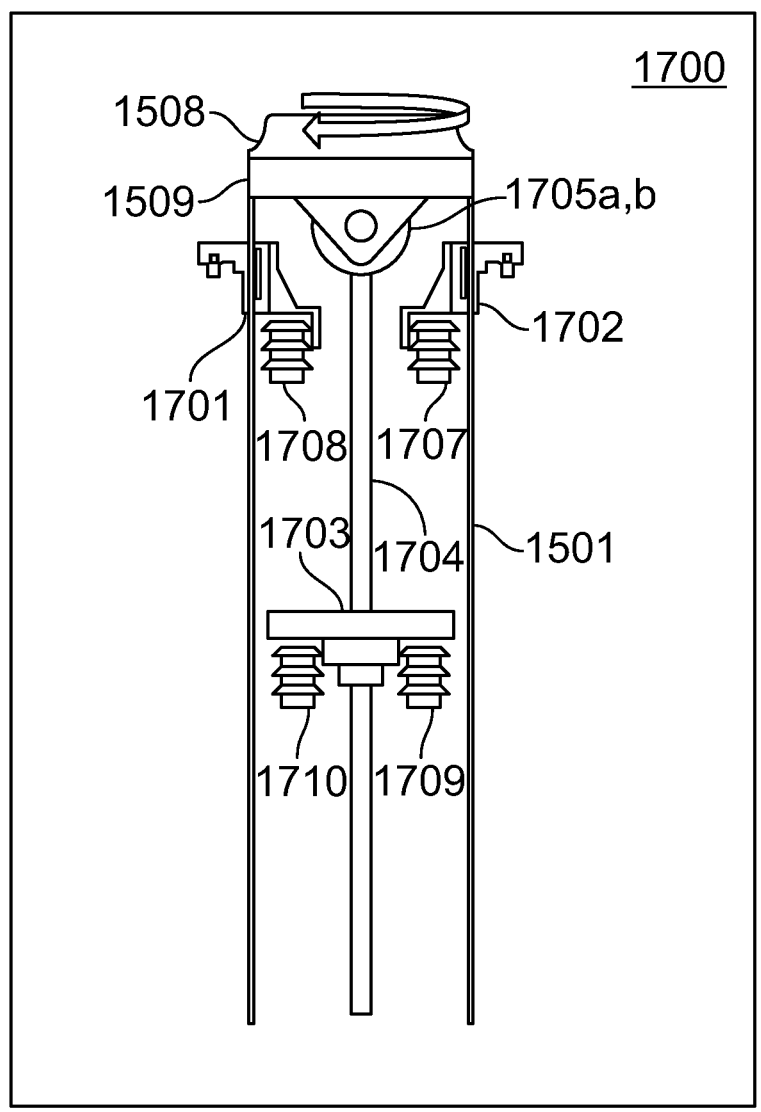
FIG. 17 shows an operational diagram of the exercise device (as shown in FIG. 15) in accordance with an embodiment.

FIG. 17 shows operational diagram 1700 of exercise device 1500 (as shown in FIG. 15) in accordance with an embodiment. Pedals 1502 and 1503 are attached to bearing mechanisms 1701 and 1702, respectively, so that pedals can travel along corresponding longitudinal openings (for example, opening 1510).

While not explicitly shown, first and second resistance bands are connected to bearing mechanisms 1701 and 1702, respectively, to mounting flange 1703 via pulleys 1705a and 1705b, respectively. The first resistance band is secured to bearing mechanism 1701 and to mounting flange by resistance band retainers 1708 and 1709, respectively, while being routed over pulley 1705a. Similarly, the second resistance band is secured to bearing mechanism 1702 and to mounting flange 1703 by resistance band retainers 1707 and 1710, respectively, while being routed over pulley 1705b.

As pedal 1502 is pushed down, bearing mechanism 1701 travels along a corresponding longitudinal opening (not explicitly shown) causing the first resistance band to stretch from mounting flange 1703 (which serves as an anchor point for the first resistance band) to bearing mechanism 1701 via pulley 1705a. The second resistance band stretches in a similar fashion as pedal 1503 is pushed down.

Tension on the first and second resistance bands may be adjusted by turning top dial 1508. Rod 1704 (which may be threaded) is secured to top dial 1508 so that as top dial 1508 is rotated, mounting flange 1703 moves up or down rod 1704. Consequently, the tension may be increased or decreased by top dial 1508 counterclockwise or clockwise.

As shown in FIG. 17, rod 1704 is passively positioned through end cap 1509 (for example, through a center hole between pulleys 1705a and 1705b).

With some embodiments, the degree of resistance may be measured by counting the number of turns that dial 1508 is rotated. For example, a counting mechanism (not explicitly shown) may increment a counter by one when dial 1508 is rotated one time counterclockwise and decrement the counter by one when dial 1508 is rotated one time clockwise. Based on the determined count, the counting mechanism may provide information to computer system 1200 (referring to FIG. 12). Based on characteristics of the resistance bands and the count information, computer system 1200 may determine an amount of work (for example, an amount of calories) that is exerted per pedal step. Consequently, computer system 1200 may report this information to a mobile app so that the mobile app can inform the user about an exercise workout.

Computer system 1200 may determine work performed by a user based on the amount of resistance provided by the resistance bands and on the distance travelled by pedaling.

Figure 18:
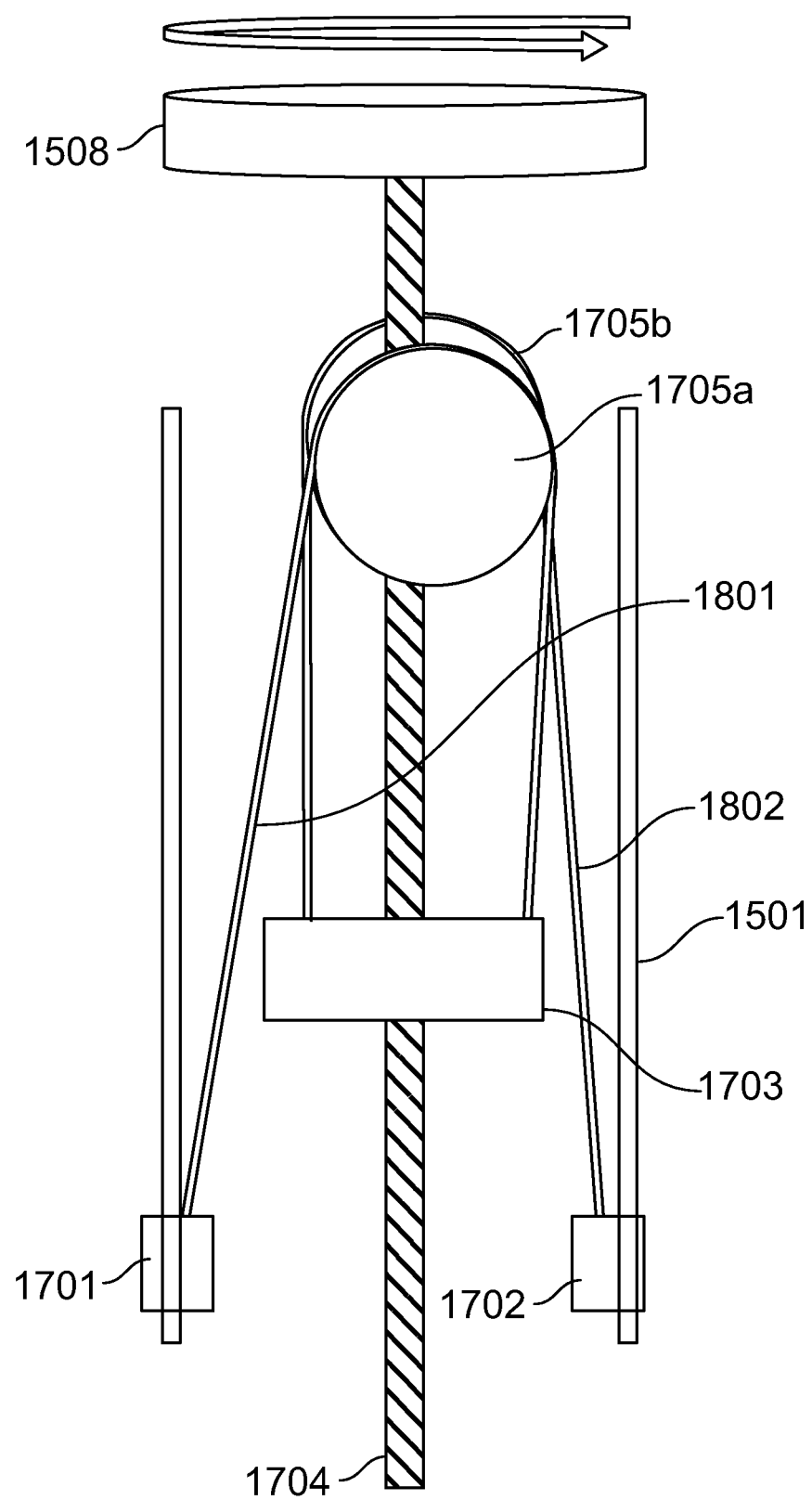
FIG. 18 shows resistance bands interacting with bearing mechanisms of the exercise device (as shown in FIG. 15) in accordance with an embodiment.

FIG. 18 shows resistance bands 1801 and 1802 interacting with bearing mechanisms 1701 and 1702, respectively, of exercise device 1500 in accordance with an embodiment.

Resistance band 1801 is anchored to mounting flange 1703 and is connected to bearing mechanism 1701 (which is attached to pedal 1502) by routing resistance band 1801 over pulley 1705a. Similarly, resistance band 1802 is anchored to mounting flange 1703 and is connected to bearing mechanism 1702 (which is attached to pedal 1503) by routing resistance band 1802 over pulley 1705b.

As previously discussed, the position of mounting flange 1703 along rod 1704 can be adjusted by rotating top dial 1508.

Figure 19:
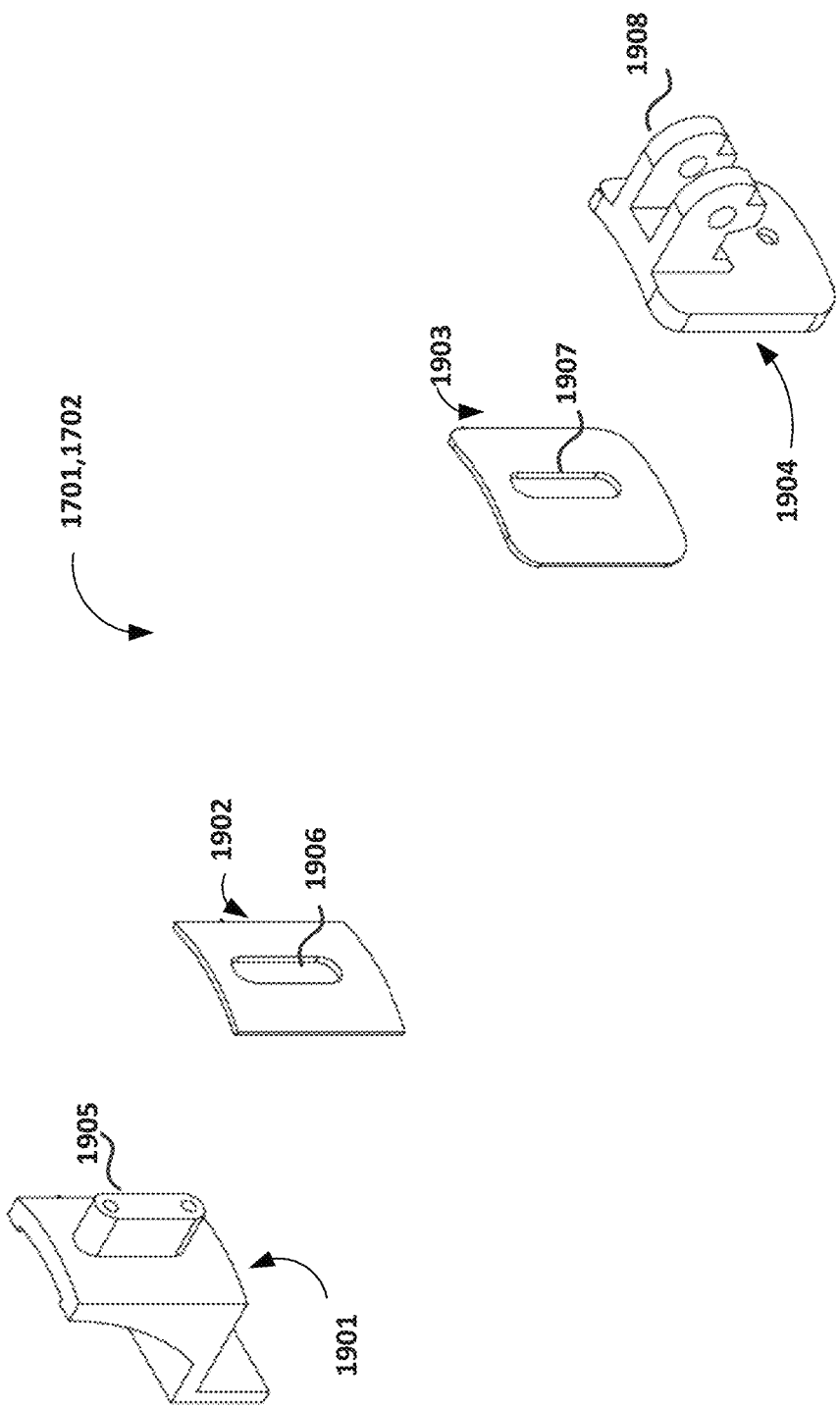
FIG. 19 shows a bearing mechanism of the exercise device (as shown in FIG. 15) in accordance with an embodiment.

FIG. 19 shows bearing mechanism 1701,1702 of exercise device 1500 in accordance with an embodiment. Bearing mechanism 1701,1702 comprises inside brace 1901, inner sliding component 1902, outer sliding component 1903, and outside brace 1904.

Inside brace 1901 has protrusion 1905 that holds bearing components 1901, 1902, 1903, and 1904 together. Protrusion 1905 is inserted through hole 1906, an longitudinal opening (for example, opening 1510 as shown in FIG. 15), and hole 1907 and is attached to outside brace 1904. As pedal 1502,1503 is pushed, inner sliding component 1902 and outer sliding component 1903 moves along friction-reducing pads as will be discussed in further detail.

Resistance band 1801,1802 (as shown in FIG. 18) may be attached to inside brace 1901 by routing resistance band 1801,1802 through a hole (not explicitly shown) of inside brace 1901, where a corresponding end of resistance band 1801,1802 is secured with resistance band retainer 1709, 1708 (as shown in FIG. 17), respectively.

Outside brace 1904 may include mating mount 1908, which enables pedal 1502 or 1503 to be attached to bearing mechanism 1701,1702.

Figure 20:
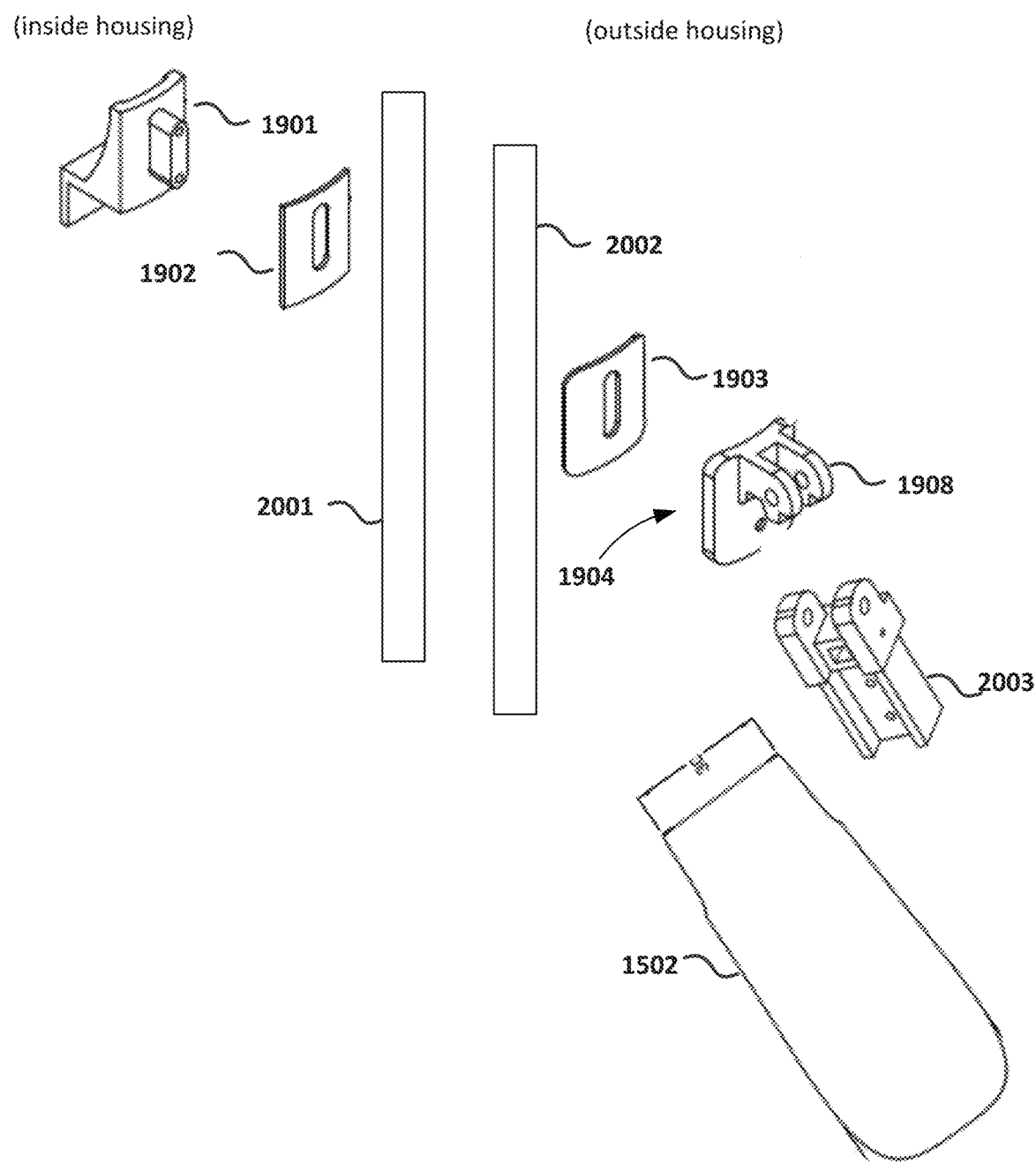
FIG. 20 shows an operational diagram of the bearing mechanism (as shown in FIG. 19) interacting with friction-reducing pads along a housing of the exercise device (as shown in FIG. 15) in accordance with an embodiment.

FIG. 20 shows operational diagram 2000 of bearing mechanism 1701,1702 (as shown in FIG. 19) interacting with friction-reducing pads 2001 and 2002 along housing 1501 of exercise device 1500 in accordance with an embodiment.

With some embodiments, as bearing mechanism 1701, 1702 travels along housing 1501, inner sliding component 1902 and outer sliding component 1903 are in contact with pads 2001 and 2002, respectively. Pads 2001 and 2002 typically comprise material that has a lower coefficient of friction than that of housing 1501. For example, pads 2001 and 2002 may be constructed from polytetrafluoroethylene (PTFE), which has non-stick properties having a small coefficient of friction between 0.05 to 0.10.

With some embodiments, bearing mechanism 1701,1702 may travel along housing 1501 with direct contact to the surface of housing 1501, thus eliminating pads 2001 and 2001

Also, as shown in FIG. 20, pedal hinge 2003 attaches pedal 1502 to bearing mechanism 1701,1702 via mating mount 1908.

Figure 21:
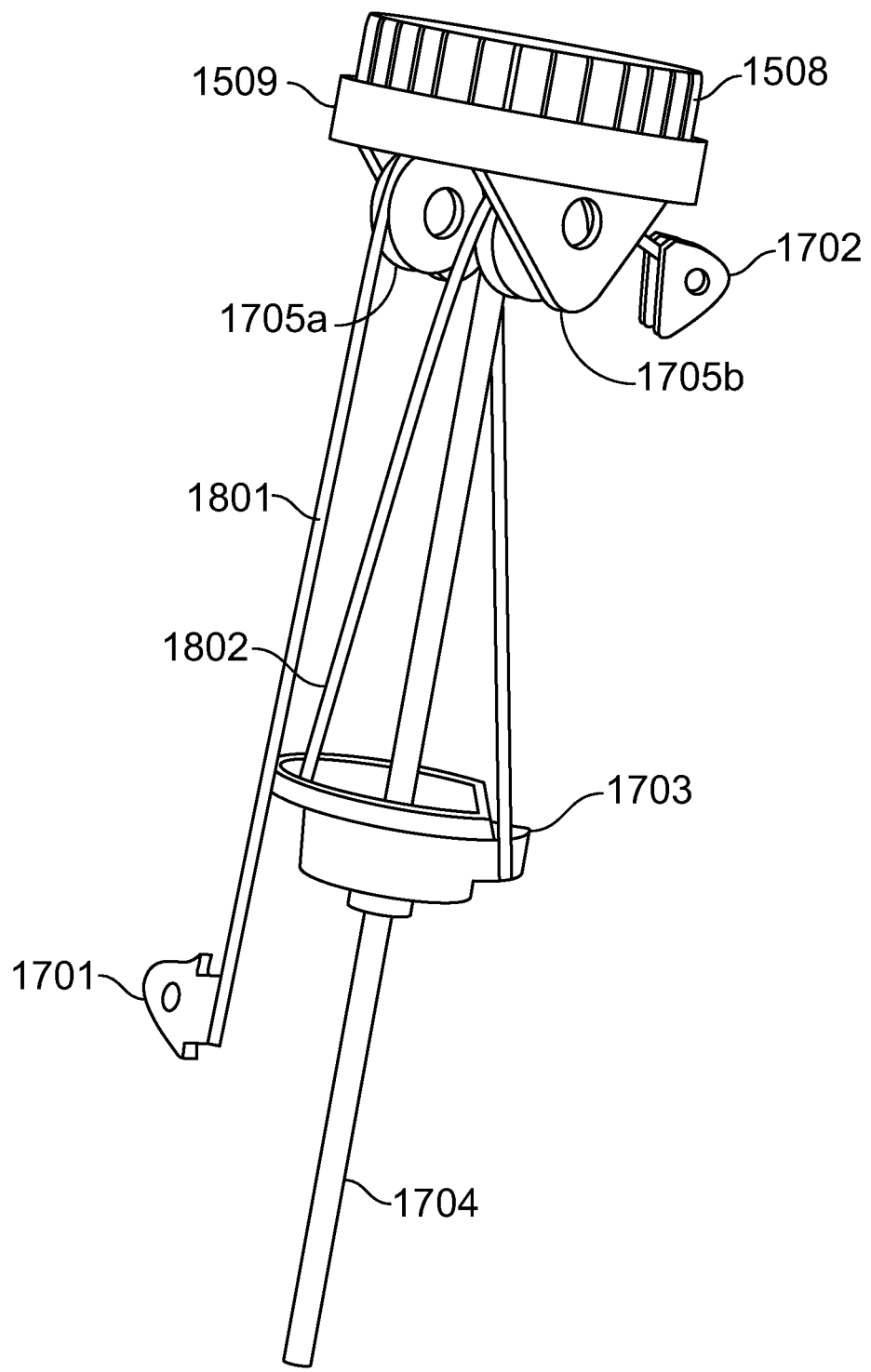
FIG. 21 shows resistance bands connected between bearings mechanisms and a mounting flange via pulleys of the exercise device (as shown in FIG. 15) in accordance with an embodiment.

FIG. 21 shows resistance bands 1801 and 1802 connected between bearings mechanisms 1701 and 1702, respectively, and mounting flange 1703 via pulleys 1705a and 1705b, respectively, of exercise device 1500 in accordance with an embodiment.

As previously discussed, the resistance provided by resistance bands 1801 and 1802 increases with the distance between mounting flange 1703 and end cap 1509. The resistance is also related to characteristics of resistance bands 1701 and 1702 where a stiffer band typically provides more resistance.

With some embodiments, different types of resistance bands may be provided in exercise device 1500 to match the capability of a user (for example, beginning, intermediate, or advanced). Resistance bands 1801 and 1802 of a particular type may be installed during manufacturing or may be changed after manufacturing.

Figure 22:
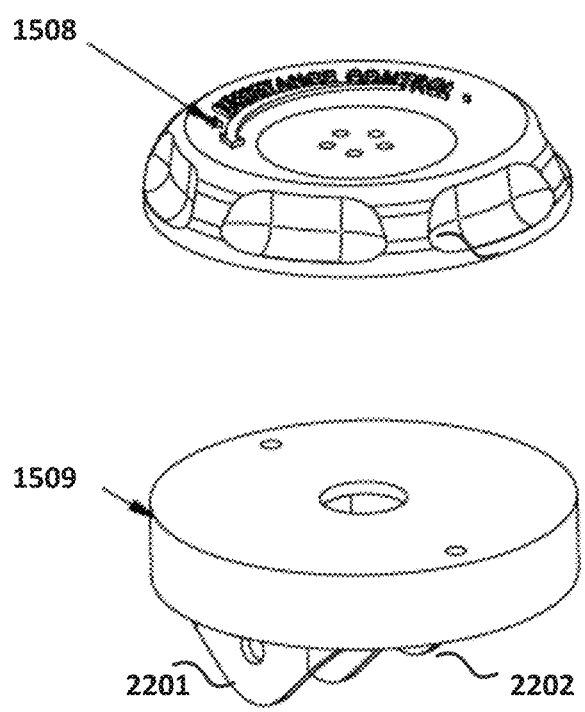
FIG. 22 shows a top dial and an end cap of the exercise device (as shown in FIG. 15) in accordance with an embodiment.

FIG. 22 shows top dial 1508 and end cap 1509 of exercise device 1500 in accordance with an embodiment. As shown in FIG. 15, top dial 1508 is situated over end cap 1509.

End cap 1509 includes pulley mounting components 2201 and 2202 for accommodating pulleys 1705a and 1705b (as shown in FIG. 17), respectively. Pulleys 1705a and 1705b may be secured in place with a pin or shaft that allows pulleys 1705a and 1705b to rotate as resistance bands 1701 and 1702 are stretched or contracted when pedals 1502 and 1503 move.

Figure 23:
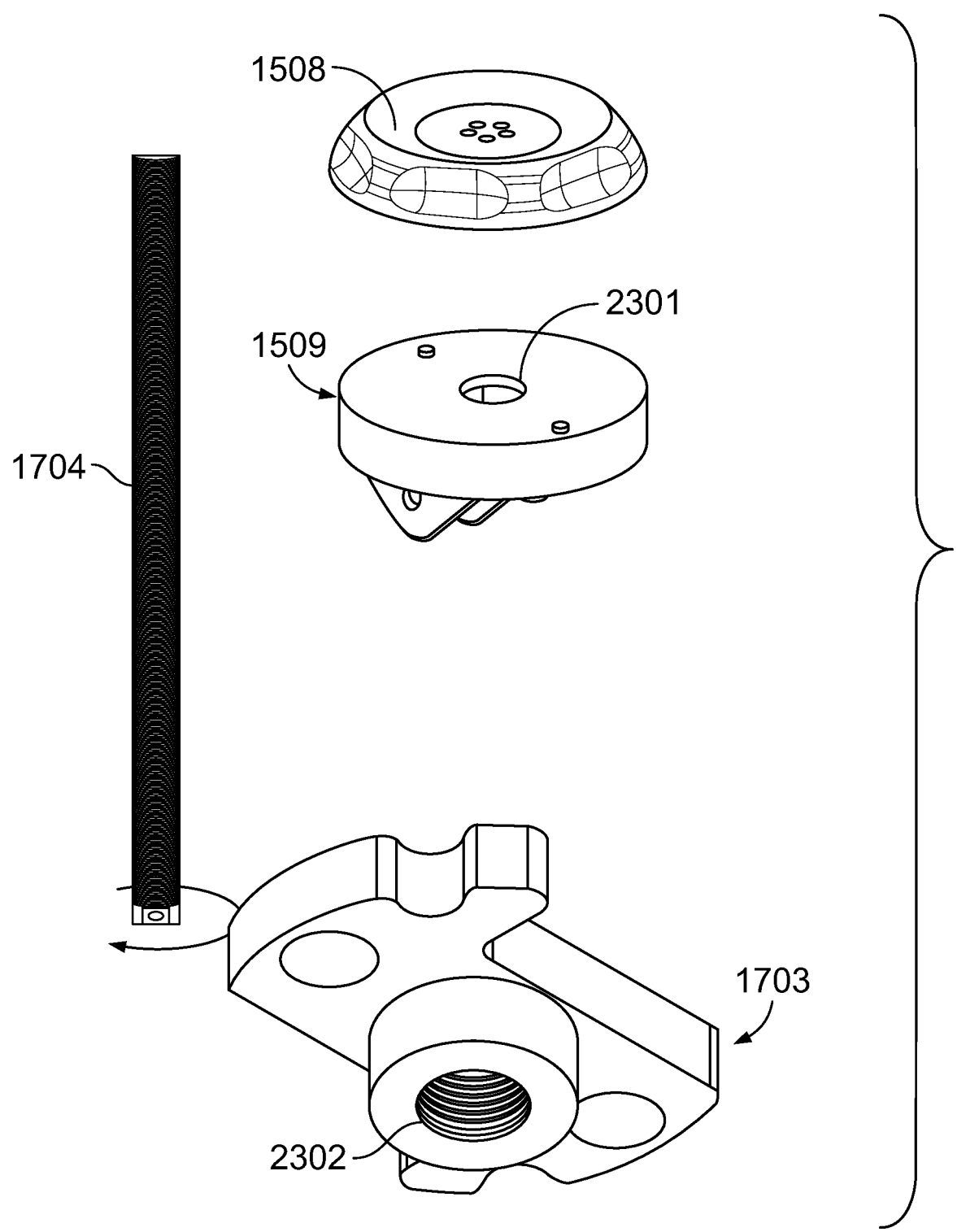
FIG. 23 shows a top dial, end cap, mounting flange, and adjusting rod of the exercise device (as shown in FIG. 15) in accordance with an embodiment.

FIG. 23 shows top dial 1508, end cap 1509, mounting flange 1703, and adjusting rod 1704 of exercise device 1500 in accordance with an embodiment. As shown in FIG. 18, an end of rod 1704 is attached to top dial 1508, Consequently, as top dial 1703 rotates, mounting flange 1703 moves up or down rod 1704.

Rod 1704 is also attached to mounting flange 1703 and is passively routed through end cap 1509 via hole 2301 (where the diameter of hole 2301 is larger than the diameter of rod 1704).

Mounting flange 1703 may be attached to rod 1704 by mating the threads of hole 2302 with the threads of rod 1704. Consequently, mounting flange 1703 moves along the threads of rod 1704 as top dial 1508 is rotated.

As can be appreciated by one skilled in the art, a computer system with an associated computer-readable medium containing instructions for controlling the computer system can be utilized to implement the exemplary embodiments that are disclosed herein. The computer system may include at least one computer such as a microprocessor, digital signal processor, and associated peripheral electronic circuitry.

Exemplary Clauses

1. A physical exercise apparatus for a user, the apparatus comprising:
   a lower cylindrical housing having first and second longitudinal oval cuts that are situated opposite of each other along the sides of the housing, a bottom edge having a desired angle, and a plurality of openings around a lower circumference;
   first and second pedals;
   first and second bearing mechanisms accommodating the first and second pedals along the first and second longitudinal oval cuts, respectively;
   the first and second bearing mechanisms comprising:
      a first pair of bearings and a second pair of bearings, respectively; and
      a first cantilever brace connected to the first pair of bearings and a second cantilever brace connected to the second pair of bearings;
   an inside bearing track that is situated within the lower cylindrical housing, the inside bearing track having first and second tracks opposite and parallel to each other;
   the first and second bearing mechanisms constrained to travel along the first and second tracks of the inside bearing track, respectively;
   the first and second pedals attached to the first and second bearing mechanisms, respectively;
   a resistance mechanism providing resistance to the first and second pedals when the first and second pedals are pushed by the user along the first and second tracks, respectively; and
   a base mechanism having a plurality of base supports, each base support attached to the lower cylindrical housing at a corresponding opening of the plurality of openings, wherein the physical exercise apparatus can be positioned at the desired angle.

2. The apparatus of clause 1, wherein the resistance mechanism comprises first and second primary resistance bands providing a minimum level of resistance to movement of the first and second pedals, respectively.

3. The apparatus of clause 2, wherein:
   the apparatus comprises an upper cylindrical housing;
   the resistance mechanism further comprises a pair of secondary resistance bands that are attached to the upper cylindrical housing; and
   the level of resistance provided by the pair of secondary resistance bands being adjustable as the upper cylindrical housing is rotated.

4. The apparatus of clause 1, wherein:
   the first and second pedals and the base supports are foldable along the lower cylindrical housing.

What is claimed is:

1. A physical exercise apparatus for a user, the physical exercise apparatus comprising:
   a housing having a first longitudinal opening that is situated along a side of the housing, a bottom edge having a desired angle, and a plurality of openings around a lower edge of the housing;
   a first lever;
   a first bearing mechanism accommodating the first lever along the first longitudinal opening;
   the first bearing mechanism comprising:
      a first inside brace having a first protrusion;
      a first inner sliding component positioned adjacent to an inside portion of the housing and having a first inner opening;
      a first outer sliding component adjacent to an outside portion of the housing and having a first outer opening;
      a first outside brace positioned outside the first outer sliding component;
      the first protrusion extending through the first inner opening, the first longitudinal opening, and the first outer opening; and
      the first outside brace attached to the first protrusion;
   the first bearing mechanism constrained to travel linearly along the first longitudinal opening;

the first lever attached to the first bearing mechanism; and
a resistance mechanism attached to the first bearing mechanism to apply resistance to the first lever when the first lever is pushed by the user along the first longitudinal opening.

2. The physical exercise apparatus of claim 1, further comprising:
a first inside friction-reducing pad and a first outside friction-reducing pad having a coefficient of friction less than that of a material of the housing,
wherein the first inside and first outside friction-reducing pads are affixed to inside and outside surfaces of the housing, respectively, and wherein the first inner and first outer sliding components are in contact with the first inside and first outside friction-reducing pads, respectively.

3. The physical exercise apparatus of claim 2, wherein the first inside friction-reducing pad and the first outside friction-reducing pad comprise polytetrafluoroethylene (PTFE).

4. The physical exercise apparatus of claim 1, wherein the first lever comprises a first handle.

5. The physical exercise apparatus of claim 1, wherein the first lever comprises a first pedal.

6. The physical exercise apparatus of claim 5, further comprising:
a first pedal hinge,
wherein the first outside brace comprises a mating mount and wherein the first pedal is connected by the first pedal hinge to the mating mount and wherein the first pedal is foldable against the housing.

7. The physical exercise apparatus of claim 5, further comprising:
a second pedal;
a second bearing mechanism accommodating the second pedal along a second longitudinal opening of the housing, wherein the second longitudinal opening is opposite the first longitudinal opening along the housing; and
the resistance mechanism attached to the second bearing mechanism to apply resistance to the second pedal when the second pedal is pushed by the user along the second longitudinal opening.

8. The physical exercise apparatus of claim 5, wherein the first pedal includes:
a pedometer configured to count a number of exercise steps exerted by the user.

9. The physical exercise apparatus of claim 8 comprising a computing device, the computing device further comprising:
a processor;
a wireless communication interface;
memory storing computer-executable instructions that, when executed by the processor, cause the computing device to:
obtain a first datum from the pedometer, wherein the first datum is indicative of the number of exercise steps exerted by the user; and
transmit a first wireless signal via the wireless communication interface to an app executing on a wireless device, wherein the first wireless signal conveys the first datum indicative of the number of exercise steps.

10. The physical exercise apparatus of claim 9 further comprising:
a measurement device configured to generate a second datum indicative of a degree of resistance presented by the resistance mechanism,
wherein the memory storing computer-executable instructions that, when executed by the processor, further cause the computing device to:
obtain the second datum from the measurement device, wherein the second datum is indicative of the degree of resistance; and
transmit a second wireless signal via the wireless communication interface to the app executing on the wireless device, wherein the second wireless signal conveys the second datum indicative of the degree of resistance.

11. The physical exercise apparatus of claim 1, further comprising:
a base mechanism having a plurality of base supports, each base support attached to the housing at a corresponding opening of the plurality of openings, wherein the physical exercise apparatus can be positioned at the desired angle.

12. The physical exercise apparatus of claim 11, wherein the base mechanism comprises a base hinge associated with each of the plurality of base supports and wherein each said base support is foldable against the housing.

13. The physical exercise apparatus of claim 1, wherein the resistance mechanism comprises:
a first pulley;
an end cap positioned at a top of the housing, wherein the end cap further comprises a pulley mounting component for positioning the first pulley;
a mounting flange; and
a first resistance band fastened to the mounting flange and the first inside brace of the first bearing mechanism via the first pulley,
wherein the first resistance band stretches as the first lever is pushed downward along the first longitudinal opening.

14. The physical exercise apparatus of claim 13, wherein the resistance mechanism comprises:
an adjusting rod;
a top dial positioned over the end cap and attached to an end of the adjusting rod; and
the adjusting rod passively positioned through the end cap and adjustably positioning the mounting flange as the top dial is rotated.

15. The physical exercise apparatus of claim 14, wherein the adjusting rod is threaded and is mated with a threaded center hole of the mounting flange.

16. The physical exercise apparatus of claim 13, further comprising:
first and second resistance band retainers;
the first resistance band retainer securing the first resistance band to the mounting flange; and
the second resistance band retainer securing the first resistance band to the first inside brace of the first bearing mechanism.

17. A physical exercise apparatus for a user, the physical exercise apparatus comprising:
a housing having first and second longitudinal openings that are situated opposite of each other along sides of the housing, a bottom edge having a desired angle, and a plurality of openings around a lower edge of the housing;
first and second pedals;
first and second bearing mechanisms accommodating the first and second pedals along the first and second longitudinal openings, respectively;
the first bearing mechanism comprising:
a first inside brace having a first protrusion;

a first inner sliding component positioned adjacent to an inside portion of the housing and having a first inner opening;

a first outer sliding component adjacent to an outside portion of the housing and having a first outer opening;

a first outside brace positioned outside the first outer sliding component;

the first protrusion extending through the first inner opening, the first longitudinal opening, and the first outer opening; and the first outside brace attached to the first protrusion;

the first and second bearing mechanisms constrained to travel along the first and second longitudinal openings, respectively;

the first and second pedals attached to the first and second bearing mechanisms, respectively;

a resistance mechanism providing resistance to the first and second pedals when the first and second pedals are pushed by the user along the first and second longitudinal openings, respectively; and the resistance mechanism comprising:

a first pulley and a second pulley;

an end cap positioned at a top of the housing, wherein the end cap further comprises a pulley mounting component for positioning the first and second pulleys;

a mounting flange;

a first resistance band and a second resistance band fastened to the mounting flange and the first inside brace of the first bearing mechanism and a second inside brace of the second bearing mechanism, respectively, wherein the first and second resistance bands stretch as the first and second pedals are pushed downward;

an adjusting rod; and a top dial positioned over the end cap and attached to an end of the adjusting rod, wherein the adjusting rod is passively positioned through the end cap and adjustably positioning the mounting flange as the top dial is rotated.

\* \* \* \* \*